US010813929B2

(12) United States Patent
Pollard et al.

(10) Patent No.: US 10,813,929 B2
(45) Date of Patent: Oct. 27, 2020

(54) TREATING CANCER WITH ATR INHIBITORS

(71) Applicant: VERTEX PHARMACEUTICALS INCORPORATED, Boston, MA (US)

(72) Inventors: John Robert Pollard, Abingdon (GB); Philip Michael Reaper, Richmond (GB)

(73) Assignee: VERTEX PHARMACEUTICALS INCORPORATED, Boston, MA (US)

( * ) Notice: Subject to any disclaimer, the term of this patent is extended or adjusted under 35 U.S.C. 154(b) by 0 days.

(21) Appl. No.: 14/193,845

(22) Filed: Feb. 28, 2014

(65) Prior Publication Data
US 2014/0356456 A1 Dec. 4, 2014

Related U.S. Application Data

(63) Continuation of application No. 13/633,114, filed on Oct. 1, 2012, now abandoned.

(60) Provisional application No. 61/542,084, filed on Sep. 30, 2011.

(51) Int. Cl.
| *A61K 31/497*   | (2006.01) |
| *A61K 31/4965*  | (2006.01) |
| *A61K 31/555*   | (2006.01) |
| *A61K 31/7048*  | (2006.01) |
| *A61K 31/7068*  | (2006.01) |
| *A61P 35/00*    | (2006.01) |
| *A61K 33/24*    | (2019.01) |
| *A61K 45/06*    | (2006.01) |
| *A61N 5/10*     | (2006.01) |

(52) U.S. Cl.
CPC ........ *A61K 31/497* (2013.01); *A61K 31/4965* (2013.01); *A61K 31/555* (2013.01); *A61K 31/7048* (2013.01); *A61K 31/7068* (2013.01); *A61K 33/24* (2013.01); *A61K 45/06* (2013.01); *A61P 35/00* (2018.01); *A61N 2005/1098* (2013.01)

(58) Field of Classification Search
CPC .................................................. A61K 31/497
See application file for complete search history.

(56) References Cited

U.S. PATENT DOCUMENTS

| 4,309,430 A | 1/1982 | Bock et al. |
| 5,143,824 A | 9/1992 | Yamakawa et al. |
| 6,469,002 B1 | 10/2002 | Ohshima et al. |
| 6,660,753 B2 | 12/2003 | Van Wagenen et al. |
| 6,790,935 B1 | 9/2004 | Mutter et al. |
| 6,858,600 B2 | 2/2005 | Hamilton et al. |
| 6,992,087 B2 | 1/2006 | Verhoest et al. |
| 7,041,672 B2 | 5/2006 | Verhoest et al. |
| 7,043,079 B2 | 5/2006 | Malvar et al. |
| 7,145,002 B2 | 12/2006 | Brands et al. |
| 7,199,123 B2 | 4/2007 | Munchhof |
| 7,277,118 B2 | 10/2007 | Foote |
| 7,385,626 B2 | 6/2008 | Aggarwal et al. |
| 7,394,926 B2 | 7/2008 | Bryll et al. |
| 7,452,993 B2 | 11/2008 | Arnold et al. |
| 7,574,131 B2 | 8/2009 | Chang et al. |
| 7,622,583 B2 | 11/2009 | Ungashe et al. |
| 7,626,021 B2 | 12/2009 | Arnold et al. |
| 7,700,601 B2 | 4/2010 | Chan et al. |
| 7,704,995 B2 | 4/2010 | Buhr et al. |
| 7,829,558 B2 | 11/2010 | Arnold et al. |
| 7,872,031 B2 | 1/2011 | Lauffer et al. |
| 7,902,197 B2 | 3/2011 | Elworthy et al. |
| 7,932,254 B2 | 4/2011 | DuBois et al. |
| 7,939,531 B2 | 5/2011 | Bamberg et al. |
| 7,981,893 B2 | 7/2011 | Mortensen et al. |
| 8,063,032 B2 | 11/2011 | Chytil et al. |
| 8,106,197 B2 | 1/2012 | Cui et al. |
| 8,410,112 B2 | 4/2013 | Charrier et al. |
| 8,492,582 B2 | 7/2013 | Yokotani et al. |
| 8,765,751 B2 | 7/2014 | Charrier et al. |
| 8,841,308 B2 | 9/2014 | Charrier et al. |
| 8,841,337 B2 | 9/2014 | Charrier et al. |
| 8,841,449 B2 | 9/2014 | Charrier et al. |
| 8,841,450 B2 | 9/2014 | Charrier et al. |

(Continued)

FOREIGN PATENT DOCUMENTS

| CN | 1551869 A | 12/2004 |
| CN | 101001606 A | 7/2007 |

(Continued)

OTHER PUBLICATIONS

Rosen et al., Premetrexed combination therapy in the treatment of non-small cell lung cancer, 2002, Semin Oncol, 2, Suppl 5, pp. 23-29.*
Wagner et al., Prospects for the Use of ATR Inhibitors to Treat Cancer, 2010, Pharmaceuticals, 3, pp. 1311-1334 (Year: 2010).*
Abdel-Magid, A., "Inhibitors of ATR Kinase for Treatment on Cancer", ACS Medicinal Chemistry Letters, 4(8), (2013), pp. 688-689.
Ammar, Y.A., et al., "3-Ethoxycarbonylmethylenequinoxalin-2-one in Heterocyclic Synthesis. Part 1: Synthesis of New Substituted and Condensed Quinoxalines", Afinidad (2005), 62, pp. 151-160.

(Continued)

*Primary Examiner* — Kortney L. Klinkel
*Assistant Examiner* — Tori Strong
(74) *Attorney, Agent, or Firm* — Dechert LLP; Andrea L. C. Reid

(57) ABSTRACT

This invention relates to methods and compositions for treating pancreatic cancer. More specifically, this invention relates to treating pancreatic cancer with certain ATR inhibitors in combination with gemcitabine and/or radiation therapy. This invention also relates to methods and compositions for treating non-small cell lung cancer. More specifically, this invention relates to treating non-small cell lung cancer with an ATR inhibitor in combination with cisplatin or carboplatin, etoposide, and ionizing radiation.

1 Claim, 33 Drawing Sheets

(56) References Cited

U.S. PATENT DOCUMENTS

| | | |
|---|---|---|
| 8,846,686 B2 | 9/2014 | Charrier et al. |
| 8,846,917 B2 | 9/2014 | Charrier et al. |
| 8,846,918 B2 | 9/2014 | Charrier et al. |
| 8,853,217 B2 | 10/2014 | Charrier et al. |
| 8,877,759 B2 | 11/2014 | Charrier et al. |
| 8,912,198 B2 | 12/2014 | Charrier et al. |
| 8,962,631 B2 | 2/2015 | Charrier et al. |
| 8,969,356 B2 | 3/2015 | Charrier et al. |
| 8,999,632 B2 | 4/2015 | Falcon et al. |
| 9,035,053 B2 | 5/2015 | Charrier et al. |
| 9,062,008 B2 | 6/2015 | Charrier et al. |
| 9,096,584 B2 | 8/2015 | Charrier et al. |
| 9,334,244 B2 | 5/2016 | Charrier et al. |
| 9,340,546 B2 | 5/2016 | Ahmad et al. |
| 9,365,557 B2 | 6/2016 | Charrier et al. |
| 9,650,381 B2 | 5/2017 | Ahmad et al. |
| 9,670,215 B2 | 6/2017 | Ahmad et al. |
| 9,701,674 B2 | 7/2017 | Charrier et al. |
| 9,718,827 B2 | 8/2017 | Ahmad et al. |
| 9,791,456 B2 | 10/2017 | Falcon et al. |
| 9,862,709 B2 | 1/2018 | Charrier et al. |
| 2002/0064314 A1 | 5/2002 | Comaniciu et al. |
| 2002/0158984 A1 | 10/2002 | Brodsky et al. |
| 2002/0180759 A1 | 12/2002 | Park et al. |
| 2002/0195563 A1 | 12/2002 | Iida et al. |
| 2003/0008882 A1 | 1/2003 | Hamilton et al. |
| 2003/0055085 A1 | 3/2003 | Wagenen et al. |
| 2003/0199511 A1 | 10/2003 | Li et al. |
| 2004/0034037 A1 | 2/2004 | Harbeson et al. |
| 2004/0075741 A1 | 4/2004 | Berkey et al. |
| 2004/0100560 A1 | 5/2004 | Stavely et al. |
| 2004/0175042 A1 | 9/2004 | Kroeker et al. |
| 2004/0180905 A1 | 9/2004 | Munchhof |
| 2004/0202382 A1 | 10/2004 | Pilu |
| 2004/0252193 A1 | 12/2004 | Higgins |
| 2004/0264793 A1 | 12/2004 | Okubo |
| 2005/0116968 A1 | 6/2005 | Barrus et al. |
| 2005/0123902 A1 | 6/2005 | Meneses et al. |
| 2005/0207487 A1 | 9/2005 | Monroe |
| 2006/0083440 A1 | 4/2006 | Chen |
| 2006/0211709 A1 | 9/2006 | Buhr et al. |
| 2007/0037794 A1 | 2/2007 | Ungashe et al. |
| 2007/0092245 A1 | 4/2007 | Bazakos et al. |
| 2007/0120954 A1 | 5/2007 | Allen et al. |
| 2007/0149547 A1 | 6/2007 | Bonnefous et al. |
| 2007/0254868 A1 | 11/2007 | Lauffer et al. |
| 2007/0270420 A1 | 11/2007 | Harbeson et al. |
| 2007/0287711 A1 | 12/2007 | Arnold et al. |
| 2008/0132698 A1 | 6/2008 | Fagnou et al. |
| 2009/0001843 A1 | 1/2009 | Enomoto et al. |
| 2009/0005381 A1 | 1/2009 | Brown et al. |
| 2009/0143410 A1 | 6/2009 | Patel |
| 2009/0215724 A1 | 8/2009 | DuBois et al. |
| 2009/0215750 A1 | 8/2009 | Bamberg et al. |
| 2009/0215785 A1 | 8/2009 | DuBois et al. |
| 2009/0215788 A1 | 8/2009 | Elworthy et al. |
| 2009/0306087 A1 | 12/2009 | Ibrahim et al. |
| 2010/0036118 A1 | 2/2010 | Arnold et al. |
| 2010/0168138 A1 | 7/2010 | DeGoey et al. |
| 2010/0204214 A1 | 8/2010 | Chytil et al. |
| 2010/0222318 A1* | 9/2010 | Charrier ............... C07D 401/14 514/210.2 |
| 2010/0233091 A1 | 9/2010 | Neumann et al. |
| 2010/0249387 A1 | 9/2010 | Inouye |
| 2011/0015231 A1 | 1/2011 | Al-Abed et al. |
| 2011/0275797 A1 | 11/2011 | Yokotani et al. |
| 2011/0288067 A1 | 11/2011 | Hendricks et al. |
| 2011/0288097 A1 | 11/2011 | Hendricks et al. |
| 2012/0025805 A1 | 2/2012 | Matsushita et al. |
| 2012/0027874 A1 | 2/2012 | Charrier et al. |
| 2012/0035407 A1 | 2/2012 | Charrier et al. |
| 2012/0035408 A1 | 2/2012 | Charrier et al. |
| 2012/0040020 A1 | 2/2012 | Charrier et al. |
| 2012/0046295 A1 | 2/2012 | Charrier et al. |
| 2012/0065247 A1 | 3/2012 | Thompson et al. |
| 2012/0115874 A1 | 5/2012 | Wang et al. |
| 2012/0122884 A1 | 5/2012 | Charrier et al. |
| 2012/0177748 A1 | 7/2012 | Charrier et al. |
| 2012/0178756 A1 | 7/2012 | Charrier et al. |
| 2013/0017273 A1 | 1/2013 | Everitt et al. |
| 2013/0018035 A1 | 1/2013 | MacCormick et al. |
| 2013/0034616 A1 | 2/2013 | Storck et al. |
| 2013/0089624 A1 | 4/2013 | Charrier et al. |
| 2013/0089625 A1 | 4/2013 | Charrier et al. |
| 2013/0089626 A1 | 4/2013 | Pollard et al. |
| 2013/0095193 A1 | 4/2013 | Charrier et al. |
| 2013/0096139 A1 | 4/2013 | Charrier et al. |
| 2013/0115310 A1 | 5/2013 | Charrier et al. |
| 2013/0115311 A1 | 5/2013 | Charrier et al. |
| 2013/0115312 A1 | 5/2013 | Charrier et al. |
| 2013/0115313 A1 | 5/2013 | Charrier et al. |
| 2013/0115314 A1 | 5/2013 | Charrier et al. |
| 2013/0172273 A1 | 7/2013 | Aizpurua Iparraguirre et al. |
| 2013/0184292 A1 | 7/2013 | Charrier et al. |
| 2014/0044802 A1 | 2/2014 | Pollard et al. |
| 2014/0107093 A1 | 4/2014 | Charrier et al. |
| 2014/0113005 A1 | 4/2014 | Charrier et al. |
| 2014/0134596 A1 | 5/2014 | Falcon et al. |
| 2014/0163000 A1 | 6/2014 | Ahmad et al. |
| 2014/0249157 A1 | 9/2014 | Ahmad et al. |
| 2015/0031661 A1 | 1/2015 | Charrier et al. |
| 2015/0051187 A1 | 2/2015 | Charrier et al. |
| 2015/0158872 A1 | 6/2015 | Charrier et al. |
| 2015/0239874 A1 | 8/2015 | Charrier et al. |
| 2015/0247866 A1 | 9/2015 | Falcon et al. |
| 2015/0274710 A1 | 10/2015 | Charrier et al. |
| 2015/0353560 A1 | 12/2015 | Ahmad et al. |
| 2015/0359797 A1 | 12/2015 | Helleday et al. |
| 2016/0030424 A1 | 2/2016 | Pollard et al. |
| 2016/0271129 A1 | 9/2016 | Charrier et al. |
| 2016/0311809 A1 | 10/2016 | Charrier et al. |
| 2016/0347754 A1 | 12/2016 | Ahmad et al. |
| 2017/0349596 A1 | 12/2017 | Ahmad et al. |
| 2018/0072735 A1 | 3/2018 | Ahmad et al. |

FOREIGN PATENT DOCUMENTS

| | | |
|---|---|---|
| CN | 101479255 A | 7/2009 |
| CN | 101537007 A | 9/2009 |
| CN | 101652354 A | 2/2010 |
| CN | 101671336 A | 3/2010 |
| CN | 103373996 A | 10/2013 |
| EP | 313724 A2 | 5/1989 |
| EP | 1217000 A1 | 6/2002 |
| EP | 2157090 A1 | 2/2010 |
| JP | 62/270623 A2 | 11/1987 |
| JP | 63/208520 A2 | 8/1988 |
| JP | 2002/072370 A | 3/2002 |
| JP | 2002/072372 A | 3/2002 |
| JP | 2002/518389 A | 6/2002 |
| JP | 2003/074370 A | 3/2003 |
| JP | 2003/516974 A | 5/2003 |
| JP | 2005/511531 A | 4/2005 |
| JP | 2005/530760 A | 10/2005 |
| JP | 2006/156445 A | 6/2006 |
| JP | 2006/516124 A | 6/2006 |
| JP | 2006/519232 A | 8/2006 |
| JP | 2006/519833 A | 8/2006 |
| JP | 2006/520794 A | 9/2006 |
| JP | 2006/521357 A | 9/2006 |
| JP | 2006526031 | 11/2006 |
| JP | 2007/524682 A | 8/2007 |
| JP | 2008/510790 A | 4/2008 |
| JP | 2008/510792 A | 4/2008 |
| JP | 2008/517945 A | 5/2008 |
| JP | 2008/525453 A | 7/2008 |
| JP | 2008/543754 A | 12/2008 |
| JP | 2009/503103 A | 1/2009 |
| JP | 2009/027904 A | 2/2009 |
| JP | 2009/530233 A | 8/2009 |
| JP | 2009/532356 A | 9/2009 |
| JP | 2009/533327 A | 9/2009 |
| JP | 2009/541247 A | 11/2009 |
| JP | 2009/541268 A | 11/2009 |

(56) References Cited

FOREIGN PATENT DOCUMENTS

| | | |
|---|---|---|
| JP | 2010/506934 A | 3/2010 |
| JP | 2010/509356 A | 3/2010 |
| JP | 2010/077286 A | 4/2010 |
| JP | 2010/513433 A | 4/2010 |
| JP | 2010/180180 A | 8/2010 |
| JP | 2011/500778 A | 1/2011 |
| JP | 2011/042639 A | 3/2011 |
| JP | 2012/508260 A | 4/2012 |
| JP | 2012/513398 A | 6/2012 |
| JP | 2012/533248 A | 12/2012 |
| JP | 2013/501720 A | 1/2013 |
| JP | 2013/505900 A | 2/2013 |
| JP | 2013/517264 A | 5/2013 |
| JP | 2013/525476 A | 6/2013 |
| JP | 2014/510072 A | 4/2014 |
| JP | 2014/518545 A | 7/2014 |
| JP | 2014/165380 A | 9/2014 |
| NZ | 593316 A | 6/2013 |
| NZ | 593969 A | 11/2013 |
| WO | 1997043267 A1 | 11/1997 |
| WO | 1998042701 A1 | 10/1998 |
| WO | WO 99/44609 A1 | 9/1999 |
| WO | 2000004014 A1 | 1/2000 |
| WO | WO 00/76982 A1 | 12/2000 |
| WO | 2001044206 A1 | 6/2001 |
| WO | 2002009648 A2 | 2/2002 |
| WO | WO 02/080899 A1 | 10/2002 |
| WO | 2003004472 A1 | 1/2003 |
| WO | 2003004475 A1 | 1/2003 |
| WO | WO 03/032971 A1 | 4/2003 |
| WO | 2003045924 A1 | 6/2003 |
| WO | 2003076422 A1 | 9/2003 |
| WO | 2003080610 A1 | 10/2003 |
| WO | 2003087057 A1 | 10/2003 |
| WO | 2003092686 A1 | 11/2003 |
| WO | 2003093297 A2 | 11/2003 |
| WO | 2003101968 A1 | 12/2003 |
| WO | 2004000318 A2 | 12/2003 |
| WO | WO 2004/000820 A2 | 12/2003 |
| WO | 2004033431 A2 | 4/2004 |
| WO | 2004055005 A1 | 7/2004 |
| WO | 2004055006 A1 | 7/2004 |
| WO | 2004080982 A1 | 9/2004 |
| WO | WO 2004/076412 A2 | 9/2004 |
| WO | 2004084813 A2 | 10/2004 |
| WO | 2004084824 A2 | 10/2004 |
| WO | 2004085409 A2 | 10/2004 |
| WO | 2004103279 A2 | 12/2004 |
| WO | WO 2004/103369 A1 | 12/2004 |
| WO | WO 2004/103991 A1 | 12/2004 |
| WO | 2005028475 A2 | 3/2005 |
| WO | WO 2005/058876 A1 | 6/2005 |
| WO | 2005079802 A1 | 9/2005 |
| WO | 2005123672 A2 | 12/2005 |
| WO | 2006015124 A2 | 2/2006 |
| WO | WO 2006/021886 A1 | 3/2006 |
| WO | 2006053342 A2 | 5/2006 |
| WO | WO 2006/047504 A1 | 5/2006 |
| WO | 2006058074 A1 | 6/2006 |
| WO | 2006067462 A1 | 6/2006 |
| WO | 2006071548 A2 | 7/2006 |
| WO | 2006075152 A1 | 7/2006 |
| WO | 2006088837 A2 | 8/2006 |
| WO | 2006114180 A1 | 11/2006 |
| WO | 2006120573 A2 | 11/2006 |
| WO | WO 2006/124874 A2 | 11/2006 |
| WO | WO 2006/135604 A2 | 12/2006 |
| WO | 2007015632 A1 | 2/2007 |
| WO | WO 2007/016674 A2 | 2/2007 |
| WO | 2007058850 A2 | 5/2007 |
| WO | 2007063012 A1 | 6/2007 |
| WO | 2007066805 A1 | 6/2007 |
| WO | 2007076360 A1 | 7/2007 |
| WO | 2007096151 A2 | 8/2007 |
| WO | 2007096764 A2 | 8/2007 |
| WO | 2007096765 A1 | 8/2007 |
| WO | WO 2007/095588 A1 | 8/2007 |
| WO | 2007102770 A1 | 9/2007 |
| WO | 2007111904 A2 | 10/2007 |
| WO | 2007126964 A2 | 11/2007 |
| WO | 2007147874 A1 | 12/2007 |
| WO | WO 2007/147746 A1 | 12/2007 |
| WO | WO 2008/025820 A1 | 3/2008 |
| WO | 2008037477 A1 | 4/2008 |
| WO | 2008038010 A1 | 4/2008 |
| WO | 2008040651 A1 | 4/2008 |
| WO | 2008060907 A2 | 5/2008 |
| WO | WO 2008/051493 A2 | 5/2008 |
| WO | 2008071456 A2 | 6/2008 |
| WO | 2008074997 A1 | 6/2008 |
| WO | 2008079291 A2 | 7/2008 |
| WO | 2008079903 A1 | 7/2008 |
| WO | 2008079906 A1 | 7/2008 |
| WO | 2008103277 A2 | 8/2008 |
| WO | 2008106692 A1 | 9/2008 |
| WO | 2008122375 A1 | 10/2008 |
| WO | 2008124850 A1 | 10/2008 |
| WO | 2008141065 A1 | 11/2008 |
| WO | 2008144463 A1 | 11/2008 |
| WO | 2008144464 A1 | 11/2008 |
| WO | 2008157191 A2 | 12/2008 |
| WO | WO 2008/156174 A1 | 12/2008 |
| WO | 2009007390 A2 | 1/2009 |
| WO | 2009012482 A2 | 1/2009 |
| WO | 2009014637 A2 | 1/2009 |
| WO | WO 2009/005638 A2 | 1/2009 |
| WO | 2009016460 A2 | 2/2009 |
| WO | 2009024825 A1 | 2/2009 |
| WO | 2009037247 A1 | 3/2009 |
| WO | 2009053737 A2 | 4/2009 |
| WO | WO 2009/099982 A1 | 8/2009 |
| WO | 2009106885 A1 | 9/2009 |
| WO | WO 2009/111280 A1 | 9/2009 |
| WO | WO 2009/115517 A2 | 9/2009 |
| WO | 2010015803 A1 | 2/2010 |
| WO | WO 2010/016005 A1 | 2/2010 |
| WO | WO 2010/017055 A2 | 2/2010 |
| WO | 2010048131 A1 | 4/2010 |
| WO | 2010054398 A1 | 5/2010 |
| WO | 2010063634 A1 | 6/2010 |
| WO | 2010068483 A2 | 6/2010 |
| WO | 2010071837 A1 | 6/2010 |
| WO | WO 2010071837 A1 * | 6/2010 ........... C07D 401/14 |
| WO | WO 2010/073034 A1 | 7/2010 |
| WO | WO 2010/075200 A1 | 7/2010 |
| WO | 2011006074 | 1/2011 |
| WO | 2011008830 A1 | 1/2011 |
| WO | WO 2011/017513 A1 | 2/2011 |
| WO | WO 2011/035855 A1 | 3/2011 |
| WO | WO 2011/044157 A1 | 4/2011 |
| WO | WO 2011/086531 A2 | 7/2011 |
| WO | 2011117145 A2 | 9/2011 |
| WO | 2011124998 A1 | 10/2011 |
| WO | 2011130689 A1 | 10/2011 |
| WO | 2011143399 A1 | 11/2011 |
| WO | 2011143419 A1 | 11/2011 |
| WO | 2011143422 A1 | 11/2011 |
| WO | 2011143423 A2 | 11/2011 |
| WO | 2011143425 A2 | 11/2011 |
| WO | 2011143426 A1 | 11/2011 |
| WO | 2011144584 A1 | 11/2011 |
| WO | 2011144585 A1 | 11/2011 |
| WO | WO 2011/138751 A2 | 11/2011 |
| WO | WO 2011143425 A2 * | 11/2011 ........... C07D 239/46 |
| WO | 2012138938 | 10/2012 |
| WO | 2012158785 A1 | 11/2012 |
| WO | 2013049726 A2 | 4/2013 |

(56) References Cited

FOREIGN PATENT DOCUMENTS

WO    WO 2013/049722 A1    4/2013
WO    WO 2013/049859 A1    4/2013

OTHER PUBLICATIONS

Charrier, J.D., et al, "Discovery of Potent and Selective Inhibitors of Ataxia Telangiesctasia Mutated and Rad3 Related (ATR) Protein Kinase as Potential Anticancer Agents" J. Med. Chem. (Mar. 17, 2011), 54(7), pp. 2320-2330 (DOI: 10.1021/jm101488z).

Charrier, J.D., et al., "Discovery of Potent and Selective Inhibitors of ATR (Ataxia Telangiectasia Mutated and Rad3 Related) as Potential Anticancer Agents", Supplementary Information, Apr. 14, 2011.

Charrier, J.D., "Discovery of potent and selective inhibitors of Ataxia Telangiectasia mutated and Rad3 related (ATR) protein kinase as potential anticancer agents", Presentation, ACS Denver 2011, Aug. 28, 2011.

Clark, B.A.J., et al., "Mass Spectrometry of Pyrroloä2, 3-Büpyrazines and Pyrazinoä2,3-Büindole", Organic Mass Spectrometry, 12(7), (1997), pp. 421-423.

Curtin, N.J., "Inhibiting the DNA damage response as a therapeutic manoeuvre in cancer", British Journal of Pharmacology, (2013), pp. 1-52.

El-Emary, T.I., "Synthesis and Biological Activity of Some New Pyrazolo[3,4-b]pyrazines", J. Chin. Chem. Soc. (2006), 53, pp. 391-401.

Fernandes, P.S., et al., "Synthesis and Biological Activity of Heterocyclic Derivatives derived from Ethyl-2-hydroxy-quinoxaline-3-carboxylate", J. Indian Chem. Soc. (1986), 63, pp. 427-429.

Finlay, M.R., et al., "Modulation of DNA repair by pharmacological inhibitors of the PIKK protein kinase family", Bioorg. Med. Chem. Letters, 22(17) (2012), pp. 5352-5359.

Fokas, E., et al., "Targeting ATR in vivo using the novel inhibitor VE-822 results in selective sensitization of pancreatic tumors to radiation", Cell Death and Disease, 3 (2012), pp. 1-5 (DOI: 10.1038/cddis.2012.181).

Fokas, E., et al., "Targeting ATR in DNA damage response and cancer therapeutics", Cancer Treatment Reviews (2013), (DOI: 10.1016/j.ctrv.2013.03.002).

Gentili, F., et al., "Alpha2-Adrenoreceptors Profile Modulation. 4. From Antagonist to Agonist Behavior", J. Med. Chem., 51(14), Jun. 25, 2008), pp. 4289-4299.

Hall-Jackson, C.A., et al., "ATR is a caffeine-sensitive, DNA-activated protein kinase with a substrate specificity distinct from DNA-PK", Oncogene, 18(48) (1999), pp. 6707-6713.

Hickson, I., et al., "Identification and Characterization of a Novel and Specific Inhibitor of the Ataxia-Telangiectasia Mutated Kinase ATM", Cancer Research (2004), 64, pp. 9152-9159.

Hilton, S., et al., "Identification and characterisation of 2-aminopyridine inhibitors of checkpoint kinase 2", Bioorg. Med. Chem., (2010) 18, pp. 707-718.

Jiang, B., et al., "Synthesis and cytotoxicity evaluation of novel indolylpyrimidiens and indolylpyrazines as potential antitummor agents", Bioorganic & Medicinal Chemistry, 9 (2001), pp. 1149-1154.

Kim, S.T., et al., "Substrate Specificities and Identification of Putative Substrates of ATM Kinase Family Members", J. Biol. Chem. (1999) 274, pp. 37538-37543.

Klicnar, J., et al., "Studien in der Chinoxalinreihe III. Syntheses, Reaktionen und ir-spektren einiger 3-hydroxy-2-carboxymethylchinoxalin-derivative", Collection Czechoslay. Chem. Commun. (1965), 30, pp. 3092-3101.

Kurasawa, Y., et al., "Revised Structure for the Product from the Reaction of 3-Hydrazinocarbonylmethylene-2-oxo-1,2,3,4-tetrahydroquinoxaline with Nitrous Acid", Chem. Pharm. Bull. (1984), 32(10), pp. 4140-4143.

Luo, H., et al., "Molecular dynamics-based self-organizing molecular field analysis on 3-amino-6-arypyrazines as the ataxia telangiectasia mutated and Rad3 related (ATR) protein kinase inhibitors", Medicinal Chemistry Research, (2013), pp. 1-12.

McKenna, G., et al., "Evaluation of the first potent and highly selective inhibitor of ATR kinase: an approach to selectively sensitize cancer cells to ionizing radiation and hypoxia", Abstract, Mar. 31, 2012.

McKenna, G., et al., "Evaluation of the first potent and highly selective inhibitor of ATR inhibitor, VE-821: an approach to selectively sensitize cancer cells to ionizing radiation and hypoxia", Poster, Mar. 31, 2012.

Middleton, F., et al., "ATR as a Therapeutic Target", Advances in DNA Repair in Cancer, Northern Institute for Cancer Research, Newcastle University (2013), pp. 211-228.

Nakamura, H., et al., "Bimodal chemiluminescence of 8-chlorostyryl-6-phenylethynylimidazopyrazinone: Large bathochromic shift caused by a styryl group at 8-position", Tetrahedron Letters, 39, (1998), pp. 301-304.

Pires, I.M., et al., "Targeting radiation-resisitant hypoxic tumour cells thorugh ATR inhibition", British Journal of Cancer, Jun. 19, 2012, pp. 1-9.

Pollard, J., "Inhibition of the DNA Damage Response Kinase, ATR, as a Promising Anti-Cancer Approach", Presentation, Mar. 8, 2012.

Qi, et al., "Chemi- and bio-luminescence of coelenterazine analogs with phenyl homologs at the C-2 position", Journal of the Chemical Society, Perkin Transactions 1: Organic and Bio-Organic Chemistry, 13, (1992), pp. 1607-1611.

Reaper, P.M., et al., "Selective Killing of ATM- or p53-deficient cancer cells through inhibition of ATR", Supplementary Information, Nature Chemical Biology, Apr. 13, 2011, DOI: 10.1038/NCHEMBIO.573.

Reaper, P.M., et al., "Selective Killing of ATM- or p53-deficient cancer cells through inhibition of ATR", Presentation, Nov. 21, 2011.

Reaper, P.M., et al., "Selective Killing of ATM- or p53-deficient cancer cells through inhibition of ATR", Presentation, Nov. 29, 2011.

Reaper, P.M., et al., "Evaluation of a potent and highly selective inhibitor of ATR kinase: an approach to selectively sensitize cancer cells to genotoxic drugs", Abstract, Mar. 31, 2012.

Reaper, P.M., et al., "Evaluation of a Potent and Highly Selective Inhibitor of ATR Kinase: An Approach to Selectively Sensitize Cancer Cells to Genotoxic Drugs", Poster, Mar. 31, 2012.

Sarkaria, J.N., et al., "Inhibition of ATM and ATR Kinase Activities by the Radiosensitizing Agent, Caffeine", Cancer Research (1999) 59, pp. 4375-4382.

Sugimoto, T., et al., "Imidazopteridines. I. Synthesis of Imidazo [1,2-c]pteridine and its Alkyl Derivatives", Bull. Chem. Soc. Japan (1977) 50(10), pp. 2744-2747.

Ward, I.M., et al., "Histone H2AX is Phosphorylated in an ATR-dependent Manner in Response to Replicational Stress", J. Biol. Chem. (2001), 51, pp. 47759-47762.

International Search Report and Written Opinion dated Jul. 19, 2011 for Application No. PCT/US2011/036246.

International Search Report and Written Opinion dated Aug. 23, 2013 for Application No. PCT/US2013/035466.

International Search Report and Written Opinion dated Apr. 23, 2013 for Application No. PCT/US2012/058127.

International Search Report and Written Opinion dated Jan. 11, 2012 for Application No. PCT/US2011/036243.

International Search Report and Written Opinion dated Oct. 12, 2011 for Application No. PCT/US2011/036239.

International Search Report and Written Opinion dated Dec. 20, 2013 for Application No. PCT/US2013/063254.

International Search Report and Written Opinion dated Dec. 28, 2011 for Application No. PCT/US2011/036245.

International Search Report and Written Opinion dated Jan. 8, 2013 for Application No. PCT/US2012/058374.

International Search Report and Written Opinion dated Jun. 28, 2011 for Application No. PCT/US2011/036242.

International Search Report and Written Opinion dated Mar. 4, 2010 for Application No. PCT/US2009/068827.

International Search Report and Written Opinion dated Mar. 15, 2010 for Application No. PCT/US2009/063922.

(56) References Cited

OTHER PUBLICATIONS

International Search Report and Written Opinion dated Jan. 30, 2013 for Application No. PCT/US2012/058117.
International Search Report and Written Opinion dated Feb. 15, 2013 for Application No. PCT/US2012/064421.
International Search Report and Written Opinion dated Jun. 17, 2011 for Application No. PCT/US2011/036214.
International Search Report and Written Opinion dated Aug. 10, 2012 for Application No. PCT/US2012/032438.
International Search Report and Written Opinion dated Nov. 12, 2012 for Application No. PCT/US2012/058121.
International Search Report and Written Opinion dated Nov. 12, 2012 for Application No. PCT/US2012/058119.
International Search Report and Written Opinion dated Feb. 1, 2013 for Application No. PCT/US2012/064426.
International Search Report and Written Opinion dated Feb. 1, 2013 for Application No. PCT/US2012/064430.
International Search Report and Written Opinion dated Feb. 26, 2013 for Application No. PCT/US2012/064433.
International Search Report and Written Opinion dated Jan. 30, 2013 for Application No. PCT/US2012/064435.
International Search Report and Written Opinion dated Feb. 27, 2014 for Application No. PCT/US2013/064920.
Non-Final Office Action dated Aug. 8, 2013 in U.S. Appl. No. 13/631,732.
Non-Final Office Action dated Aug. 8, 2013 in U.S. Appl. No. 13/631,727.
Adamczyk et al., Synthesis of 3,7-dihydroimidazo[1,2a]pyrazine-3-ones and their chemiluminescent properties. Tetrahedron. 2003;59(41):8129-42.
Bracher et al., Total Synthesis of the Indolizidinium Alkaloid Ficuseptine. Eur J Org Chem. 2002:2288-91.
Buscemi et al., DNA damage-induced cell cycle regulation and function of novel Chk2 phosphoresidues. Mol Cell Biol. Nov. 2006;26(21):7832-45. Epub Aug. 28, 2006.
Caira, Crystalline Polymorphism of Organic Compounds. Topics in Current Chemistry. Design of Organic Solids. 1998;198:163-208.
Campone et al., Phase I and pharmacokinetic trial of AP5346, a DACH-platinum-polymer conjugate, administered weekly for three out of every 4 weeks to advanced solid tumor patients. Cancer Chemother Pharmacol. Sep. 2007;60(4):523-33. Epub Feb. 17, 2007.
Chen et al., Development of biomarker of ATR activity in surrogate human tissues. Newcastle University. Poster. Nov. 2012. 1 page.
Chen et al., Targeting the S and G2 checkpoint to treat cancer. Drug Discov Today. Mar. 2012;17(5-6):194-202. doi: 10.1016/j.drudis.2011.12.009. Epub Dec. 15, 2011.
Curtin, Inhibiting the DNA damage response as a therapeutic manoeuvre in cancer. Br J Pharmacol. Aug. 2013;169(8):1745-65. doi: 10.1111/bph.12244.
Darabantu et al., Synthesis of new polyaza heterocycles. Part 42: Diazines. Tetrahedron. 2005;61(11):2897-905.
De Wergifosse et al., Coelenterazine: a two-stage antioxidant in lipid micelles. Free Radical Biol Med. 2004;36(3):278-87.
Dias et al., Synthesis of 2,6-diphenylpyrazine derivatives and their DNA binding and cytotoxic properties. Eur J Med Chem. 2005;40:1206-13.
Erickson et al., Structure-guided expansion of kinase fragment libraries driven by support vector machine models. Biochim Biophys Acta. Mar. 2010;1804(3):642-52. doi: 10.1016/j.bbapap.2009.12.002. Epub Dec. 11, 2009.
Goto et al.,Squid bioluminescence I. Structure of watasenia oxyluciferin, a possible light-emitter in the bioluminescence of watasenia scintillans. Tetrahedron Lett. 1974;15(26):2321-4.
Hart et al., Renilla Reinformis Bioluminescence: Luciferase-Catalyzed Production of Nonradiating Excited States from Luciferin Analogues and Elucidation of the Excited State Species Involved in Energy Transfer to Renilla Green Fluorescent Protein. Biochemistry. 1979;18:2204-10.
Hilfiker et al., Relevance of Solid-state Properties for Pharmaceutical Products. Polymorphism: in the Pharmaceutical Industry. 2006;1-19.
Hirano et al., Bioluminescent properties of fluorinated semi-synthetic aequorins. Tetrahedron Lett. 1998;39(31):5541-4.
Jia et al., A Facile Preparation of 2,6-Diarylpyrazines. Heteroatom Chemistry. 1998;9(3):341-5.
Jones et al., A Suzuki Coupling Approach to Pyrazines Related to Coelenterazine. Synlett. 1996;(6):509-10.
Kao et al., Inhibition of λ-H2AX after ionizing radiation as a biological surrogate of impaired upstream DNA damage signaling and radiosensitivity. J Cancer Mol. 2010;5(2):49-54.
Lima et al., Bioisosterism: a useful strategy for molecular modification and drug design. Curr Med Chem. 2005;12(1):23-49.
Ling et al., Mechanism of Cell Cycle G2/M Arrest in Human Gastric Cancer BGC823 Cells Induced by Diallyl Disulfide. Chinese J Clin Oncol. Feb. 28, 2010;(3):121-5.
Liu et al., Chemical Biology Foundation. Science Press. Sep. 30, 2010;213-8.
Middleton et al., ATR as a Therapeutic Target. Cancer Drug Discovery and Development. 2013. Author's Proof. 20 pages.
Middleton et al., Chemosensitisation by, and Single Agent Activity of, ATR Inhibitor VE-821 in Human Breast Cancer Cells. Eur J Canc. Nov. 1, 2012;85-6.
Muslimovic et al., An optimized method for measurement of gamma-H2AX in blood mononuclear and cultured cells. Nat Protoc. 2008;3(7):1187-93. doi: 10.1038/nprot.2008.93.
Nowotnik et al., ProLindac (AP5346): a review of the development of an HPMA DACH platinum Polymer Therapeutic. Adv Drug Deliv Rev. Nov. 12, 2009;61(13):1214-9. doi: 10.1016/j.addr.2009.06.004. Epub Aug. 9, 2009. Review.
Patani et al., Bioisosterism: A Rational Approach in Drug Design. Chem Rev. Dec. 19, 1996;96(8):3147-76.
Prevo et al., The novel ATR inhibitor VE-821 increases sensitivity of pancreatic cancer cells to radiation and chemotherapy. Cancer Biol Ther. Sep. 2012;13(11):1072-81. doi: 10.4161/cbt.21093. Epub Jul. 24, 2012.
Reaper, et al., Selective killing of ATM- or p53-deficient cancer cells through inhibition of ATR. Nat Chem Biol. Apr. 13, 2011;7(7):428-30. doi: 10.1038/nchembio.573. Supplementary Information.
Redon et al., λ-H2AX as a biomarker of DNA damage induced by ionizing radiation in human peripheral blood lymphocytes and artificial skin. Adv Space Res. 2009;43(8):1171-8.
Registry (STN), 2004, RN 726138-31-4.
Richards et al., An Autoinhibitory Tyrosine Motif in the Cell-Cycle-Regulated Nek7 Kinase is Released through Binding of Nek9. Molec Cell. 2009;36:560-70.
Schultheiss et al., Facile Synthesis of Diarylpyrazines Using Suzuki Coupling of Dichloropyrazines with Aryl Boronic Acids. Heterocycles. 2003;60(8):1891-7.
Sevilla et al., Microwave-assisted synthesis of 1,3-dihydro-[1,2,5]thiadiazolo[3,4-b]pyrazine-2,2-dioxides. Tetrahedron Letters. 2006;47(48):8603-6.
Shimomura et al., Semi-synthetic aequorins with improved sensitivity to Ca2+ ions. Biochem J. Aug. 1, 1989;261(3):913-20.
Teranishi et al., Synthesis and Chemiluminescence of Coelenterazine (Oplophorus Luciferin) Analogues . Bulletin Chem Soc Japan. 1990;63(11):3132-40.
Tutin, CCLVII.-Syntheses in the epinephrine series. Part II. The formation and properties of some 2 : 5- and 2 : 6-substituted pyrazines and their conversion into amino-ketones and imino-diketones. J Chem Soc Trans. 1910;97:2495-524.
Vicent, Polymer Anticancer Ding Conjugates: Use as Single Agents and as Combination Therapy. 2007 AACR Annual Meeting. Apr. 14-18, 2007:56-62.
Wu et al., Chemi- and bioluminescence of coelenterazine analogues with a conjugated group at the C-8 position. Tetrahedron Lett. 2001;42(16):2997-3000.
U.S. Appl. No. 13/106,476, filed May 12, 2011, Charrier et al.
U.S. Appl. No. 14/816,432, filed Aug. 3, 2015, Pollard et al.
U.S. Appl. No. 14/678,489, filed Apr. 3, 2015, Charrier et al.
U.S. Appl. No. 14/633,394, filed Feb. 27, 2015, Falcon et al.
U.S. Appl. No. 13/106,184, filed May 12, 2011, Charrier et al.

(56) References Cited

OTHER PUBLICATIONS

U.S. Appl. No. 14/562,965, filed Dec. 8, 2014, Charrier et al.
U.S. Appl. No. 14/223,109, filed Mar. 24, 2014, Charrier et al.
U.S. Appl. No. 14/467,175, filed Aug. 25, 2014, Charrier et al.
PCT/US2011/036246, Jul. 19, 2011, International Search Report and Written Opinion.
PCT/US2012/035466, Aug. 23, 2013, International Search Report and Written Opinion.
PCT/US2012/058127, Apr. 23, 2013, International Search Report and Written Opinion.
PCT/US2011/036243, Jan. 11, 2012, International Search Report and Written Opinion.
PCT/US2011/036239, Oct. 12, 2012, International Search Report and Written Opinion.
PCT/US2013/063254, Dec. 20, 2013, International Search Report and Written Opinion.
PCT/US2011/036245, Dec. 28, 2011, International Search Report and Written Opinion.
PCT/US2012/058374, Jan. 8, 2013, International Search Report and Written Opinion.
PCT/US2011/036242, Jun. 28, 2011, International Search Report and Written Opinion.
PCT/US2009/068827, Mar. 4, 2010, International Search Report and Written Opinion.
PCT/US2009/063922, Mar. 15, 2010, International Search Report and Written Opinion.
PCT/US2012/058117, Jan. 30, 2013, International Search Report and Written Opinion.
PCT/US2012/064421, Feb. 15, 2013, International Search Report and Written Opinion.
PCT/US2011/036214, Jun. 17, 2011, International Search Report and Written Opinion.
PCT/US2012/032438, Aug. 10, 2012, International Search Report and Written Opinion.
PCT/US2012/058121, Nov. 12, 2012, International Search Report and Written Opinion.
PCT/US2012/058119, Nov. 12, 2012, International Search Report and Written Opinion.
PCT/US2012/064426, Feb. 1, 2013, International Search Report and Written Opinion.
PCT/US2012/064430, Feb. 1, 2013, International Search Report and Written Opinion.
PCT/US2012/064433, Feb. 26, 2013, International Search Report and Written Opinion.
PCT/US2012/064435, Jan. 30, 2013, International Search Report and Written Opinion.
PCT/US2013/064920, Feb. 27, 2014, International Search Report and Written Opinion.
The relevance of CN1551869 is understood from its English-language abstract.
The relevance of CN101001606 is understood from its English-language abstract.
The relevance of CN101479255 is understood from its English-language abstract.
The relevance of CN101537007 is understood from its English-language abstract.
The relevance of CN101671336 is understood from its English-language abstract.
The relevance of CN103373996 is understood from its English-language abstract.
The relevance of JP2002-072370 is understood from its English-language abstract.
The relevance of JP2002-072372 is understood from its English-language abstract.
The relevance of JP2002-518389 is understood from its English-language abstract.
The relevance of JP2003-074370 is understood from its English-language abstract.
The relevance of JP2003-516974 is understood from its English-language abstract.
The relevance of JP2005-511531 is understood from its English-language abstract.
The relevance of JP2005-530760 is understood from its English-language abstract.
The relevance of JP2006-156445 is understood from its English-language abstract.
The relevance of JP2006-516124 is understood from its English-language abstract.
The relevance of JP2006-519232 is understood from its English-language abstract.
The relevance of JP2006-519833 is understood from its English-language abstract.
The relevance of JP2006-520794 is understood from its English-language abstract.
The relevance of JP2006-521357 is understood from its English-language abstract.
The relevance of JP2007-524682 is understood from its English-language abstract.
The relevance of JP2008-510790 is understood from its English-language abstract.
The relevance of JP2008-510792 is understood from its English-language abstract.
The relevance of JP2008-517945 is understood from its English-language abstract.
The relevance of JP2008-525453 is understood from its English-language abstract.
The relevance of JP2008-543754 is understood from its English-language abstract.
The relevance of JP2009-027904 is understood from its English-language abstract.
The relevance of JP2009-503103 is understood from its English-language abstract.
The relevance of JP2009-530233 is understood from its English-language abstract.
The relevance of JP2009-532356 is understood from its English-language abstract.
The relevance of JP2009-533327 is understood from its English-language abstract.
The relevance of JP2009-541247 is understood from its English-language abstract.
The relevance of JP2009-541268 is understood from its English-language abstract.
The relevance of JP2010-077286 is understood from its English-language abstract.
The relevance of JP2010-180180 is understood from its English-language abstract.
The relevance of JP2010-506934 is understood from its English-language abstract.
The relevance of JP2010-509356 is understood from its English-language abstract.
The relevance of JP2010-513433 is understood from its English-language abstract.
The relevance of JP2011-042639 is understood from its English-language abstract.
The relevance of JP2011-500778 is understood from its English-language abstract.
The relevance of JP2012-508260 is understood from its English-language abstract.
The relevance of JP2012-513398 is understood from its English-language abstract.
The relevance of JP2012-533248 is understood from its English-language abstract.
The relevance of JP2013-501720 is understood from its English-language abstract.
The relevance of JP2013-505900 is understood from its English-language abstract.
The relevance of JP2013-517264 is understood from its English-language abstract.
The relevance of JP2013-525476 is understood from its English-language abstract.
The relevance of JP2014-165380 is understood from its English-language abstract.

(56) References Cited

OTHER PUBLICATIONS

The relevance of JP2014-510072 is understood from its English-language abstract.
The relevance of JP2014-518545 is understood from its English-language abstract.
The relevance of JP62-270623 is understood from its English-language abstract.
The relevance of JP63-208520 is understood from its English-language abstract.
The relevance of NZ593316 is understood from its English-language abstract.
The relevance of NZ593969 is understood from its English-language abstract.
The relevance of WO2004/103991 is understood from its English-language abstract.
The relevance of WO2008/156174 is understood from its English-language abstract.
The relevance of WO2011/035855 is understood from its English-language abstract.
The relevance of "Liu et al." is understood by the chemical structures.
The relevance of "Ling et al." is understood from its English-language abstract.
Katritzky, A.R., et al., "Efficient synthesis of 3,5-functionalized isoxazoles and isoxazolines via 1,3-dipolar cycloaddition reactions of 1-propargyl- and 1-allylbenzotriazoles", J. Heterocyclic Chem., 37(6), (2000), pp. 1505-1510.
Kumpaty, H.J., et al., "Synthesis of N-Methyl Secondary Amines", Synth. Commun., 33(8), (2003), pp. 1411-1416.
March, J., March's Advanced Organic Chemistry, 2007, John Wiley and Sons, Chapter 16.
Wuts, P.G.M., Greene's Protective Groups in Organic Synthesis, 4th Edition, 2006, John Wiley and Sons, Chapter 4.
Wuts, P.G.M., Greene's Protective Groups in Organic Synthesis, 4th Edition, 2006, John Wiley and Sons, Chapter 7.
Saito, R., et al., "Synthesis and in vitro evaluation of botryllazine B analogues as a new class of inhibitor against human aldose reductase", Tetrahedron, 65 (2009), pp. 3019-3026.
Non-Final Office Action dated Sep. 28, 2013 in U.S. Appl. No. 13/631,727.
Non-Final Office Action dated Sep. 28, 2013 in U.S. Appl. No. 13/631,732.
Bastin et al., Salt Selection and Optimisation Procedures for Pharmaceutical New Chemical Entities. Organic Process Research and Development. American Chemical Society. 2000;4(5):427-35.
Biss et al., Selective tumor killing based on specific DNA-damage response deficiencies. Cancer Biology & Therapy. Mar. 2012; 239-46.
Kumar et al., Salt selection in drug development. Pharmaceutical Technology. 2008;32(3):128-46.
Peasland et al., Identification and evaluation of a potent novel ATR inhibitor, NU6027, in breast and ovarian cancer cell lines. British Journal of Cancer. Jul. 2011; 105(3):372-81.
Serajuddin, Salt formation to improve drug solubility. Advanced Drug Delivery Reviews. 2007; 59(7):603-16.
Brittain, editor. Polymorphism in pharmaceutical solids. CRC Press; 2009, Chapters 7 (p. 233-281) and 12 (p. 436-480).
Hancock et al., Characteristics and significance of the amorphous state in pharmaceutical systems. J Pharm Sci. Jan. 1997;86(1):1-12.
Pollard et al. Defining optimal dose schedules for ATR inhibitors in combination with DNA damaging drugs: Informing clinical studies of VX-970, the first-in-class ATR inhibitor. Proceedings: AACR Annual Meeting. Apr. 16-20, 2016.
Morgan et al., 2010, "Mechanism of radiosensitization by the Chk1/2 inhibitor AZD7762 involves abrogation of the G2 checkpoint and inhibition of homologous recombinational DNA repair." Cancer Res. 70(12):4972-81.
No Author Listed, "Brief course of molecular pharmacology," P.V. Sergeev, ed., 1975, p. 10.
Cholodov et al., "Clinical pharmacokinetics." Medicine, 1985, pp. 83-98, 134-138, 160, 378-380.
Yokoi et al., "Hypoxia Increases Resistance of Human Pancreatic Cancer Cells to Apoptosis Induced by Gemcitabine," Clinical Cancer Research, 2004, vol. 10, pp. 2299-2306.
Shibamoto et al., "Radiosensitivity of Human Pancreatic Cancer Cells In Vitro and In Vivo, and the Effect of a New Hypoxic Cell Sensitizer, Doranidazole," Radiother Oncol, 2000, vol. 56, No. 2, pp. 265-270, Abstract.
U.S. Appl. No. 15/967,110 of Charrier et al., filed Apr. 30, 2018.
U.S. Appl. No. 15/608,630 of Charrier et al., filed May 30, 2017.
U.S. Appl. No. 15/849,241 of Charrier et al., filed Dec. 20, 2017.
U.S. Appl. No. 15/633,477 of Ahmad et al., filed Jun. 26, 2017.
U.S. Appl. No. 15/763,366 of Pollard et al., filed Mar. 26, 2018.
U.S. Appl. No. 15/693,521 of Falcon et al., filed Sep. 1, 2017.

\* cited by examiner

A

B

C

D

A

B

B

B

MRC5

MRC5

A

0h

Control 822 (40nM)

12h after 6Gy

Control 822 (40nM)

A

TREATING CANCER WITH ATR INHIBITORS

CROSS REFERENCE TO RELATED APPLICATIONS

The present application is a continuation of U.S. patent application Ser. No. 13/633,114, filed on Oct. 1, 2012, which claims the benefit of U.S. provisional application No. 61/542,084 filed on Sep. 30, 2011, the entire contents of each of which are incorporated herein by reference.

BACKGROUND OF THE INVENTION

Pancreatic cancer is the tenth most common site of new cancers and is responsible for 6% of all cancer related deaths. The 5-year survival rate is less than 5%.

Current therapies involve either neoadjuvant treatment with chemotherapy (e.g., with gemcitabine) and/or radiation therapy or surgical removal followed by either adjuvant chemotherapy (e.g., with gemcitabine) or radiation therapy. Although the survival rate with treatment of gemcitabine increases the 5-year survival from 10% to 20%, there still is a strong need for better therapies for treating pancreatic cancer.

Several therapeutics have been tested in phase II and phase III trials though results have not been too promising. Tipifarnib, an oral farnesyltransferase inhibitor, did not show significant improvement in overall survival when combined with gemcitabine. Similarly, cetuximab, an epidermal growth factor receptor (EGRF), also showed no clinical benefit when combined with gemcitabine. Only a small increase in overall survival (6.24 months versus 5.91 months) was observed.

Lung cancer is the second most common form of cancer and is the leading cause of cancer-related mortality. Non-small cell lung cancer (NSCLC) is the most common form of lung cancer, accounting for about 85% of all lung cancer cases. Most patients present with advanced stage III or IV NSCLC with a 5-year survival of 24% and 4% respectively. Because of the advanced nature of disease on presentation, surgical resection is often not an option. For the majority of patients therapy involves chemotherapy and/or radiation treatment. The selection of chemotherapy is highly variable based on disease stage, patient performance criteria and geographical regional preference. In most cases chemotherapy is based on a doublet that includes a platinating agent such as Cisplatin or carboplatin and a second cytotoxic drug such as gemcitabine, etoposide or taxotere. For a small number of patients, therapy can include treatment with agents that target specific proteins that are mutated or disregulated such as ALK and EGFR (eg crizotinib, gefitinib and erlotinib). Patients are selected for these targeted treatments based on genetic or proteomic markers. A great number of agents have been assessed in late stage NSCLC clinical studies, however most have shown very little benefit over chemotherapy based treatments, with median overall survival typically less than 11 months.

Accordingly, there is a tremendous need for new strategies to improve pancreatic and non-small cell lung cancer treatments.

ATR ("ATM and Rad3 related") kinase is a protein kinase involved in cellular responses to certain forms of DNA damage (eg double strand breaks and replication stress). ATR kinase acts with ATM ("ataxia telangiectasia mutated") kinase and many other proteins to regulate a cell's response to double strand DNA breaks and replication stress, commonly referred to as the DNA Damage Response ("DDR"). The DDR stimulates DNA repair, promotes survival and stalls cell cycle progression by activating cell cycle checkpoints, which provide time for repair. Without the DDR, cells are much more sensitive to DNA damage and readily die from DNA lesions induced by endogenous cellular processes such as DNA replication or exogenous DNA damaging agents commonly used in cancer therapy.

Healthy cells can rely on a host of different proteins for DNA repair including the DDR kinases ATR and ATM. In some cases these proteins can compensate for one another by activating functionally redundant DNA repair processes. On the contrary, many cancer cells harbour defects in some of their DNA repair processes, such as ATM signaling, and therefore display a greater reliance on their remaining intact DNA repair proteins which include ATR.

In addition, many cancer cells express activated oncogenes or lack key tumour suppressors, and this can make these cancer cells prone to dysregulated phases of DNA replication which in turn cause DNA damage. ATR has been implicated as a critical component of the DDR in response to disrupted DNA replication. As a result, these cancer cells are more dependent on ATR activity for survival than healthy cells. Accordingly, ATR inhibitors may be useful for cancer treatment, either used alone or in combination with DNA damaging agents, because they shut down a DNA repair mechanism that is more important for cellular survival in many cancer cells than in healthy normal cells.

In fact, disruption of ATR function (e.g. by gene deletion) has been shown to promote cancer cell death both in the absence and presence of DNA damaging agents. This suggests that ATR inhibitors may be effective both as single agents and as potent sensitizers to radiotherapy or genotoxic chemotherapy.

Furthermore, solid tumors often contain regions that are hypoxic (low oxygen levels). This is significant because hypoxic cancer cells are known to be resistant to treatment, most notably IR treatment, and are highly aggressive. One reason for this observation is that components of the DDR can be activated under hypoxic conditions and it has also been shown that hypoxic cells are more reliant on components of the DDR for survival.

For all of these reasons, there is a need for the development of potent and selective ATR inhibitors for the treatment of pancreatic cancer, for the treatment of lung cancer, and for the development of agents that are effective against both hypoxic and normoxic cancer cells.

SUMMARY OF THE INVENTION

This invention relates to uses of ATR inhibitors for treating pancreatic cancer and non-small cell lung cancer. With respect to pancreatic cancer, this invention relates to methods of treating pancreatic cancer in a patient (e.g., a human) with an ATR inhibitor in combination with gemcitabine and/or radiation therapy. Applicants have demonstrated synergistic efficacy of ATR inhibitors in combination with gemcitabine and/or radiation therapy in clonogenic and viability assays on the pancreatic cancer cell lines, (e.g. PSN-1, MiaPaCa-2 and Panc-1) as well as in a primary tumor line (e.g., Panc-M). Disruption of ATR activity was measured by assessing DNA damage induced phosphorylation of Chk1 (Ser 345) and by assessing DNA damage foci and RAD51 foci following irradiation.

With respect to non-small cell lung cancer, his invention relates to methods of treating non-small cell lung cancer with an ATR inhibitor in combination with cisplatin or carboplatin, etoposide, and ionizing radiation. Applicants have demonstrated synergy of ATR inhibitors in combination with cisplatin, etoposide, gemcitabine, oxaplatin and irinotecan in viability assays against a panel of 35 human lung cancer cell lines as well as demonstrated in vivo efficacy in a lung cancer mouse model in combination with cisplatin.

MiaPaca cells were plated at low densities and drug was added at various time points in relation to the 4 Gy radiation treatment: 1 h prior to IR, 5 min after IR, 2 h or 4 h after IR; and removed at various time points. 5 min after, 1 h after, or 19 h after IR. Clonogenic survival was assessed after 14 days. Results are shown as the surviving fraction at 4 Gy (top panel) or the percentage radiosensitisation (middle panel) compared to the DMSO-treated cells. The different treatment schedules did not cause differences in plating efficiency (bottom panel).

Figure 11:
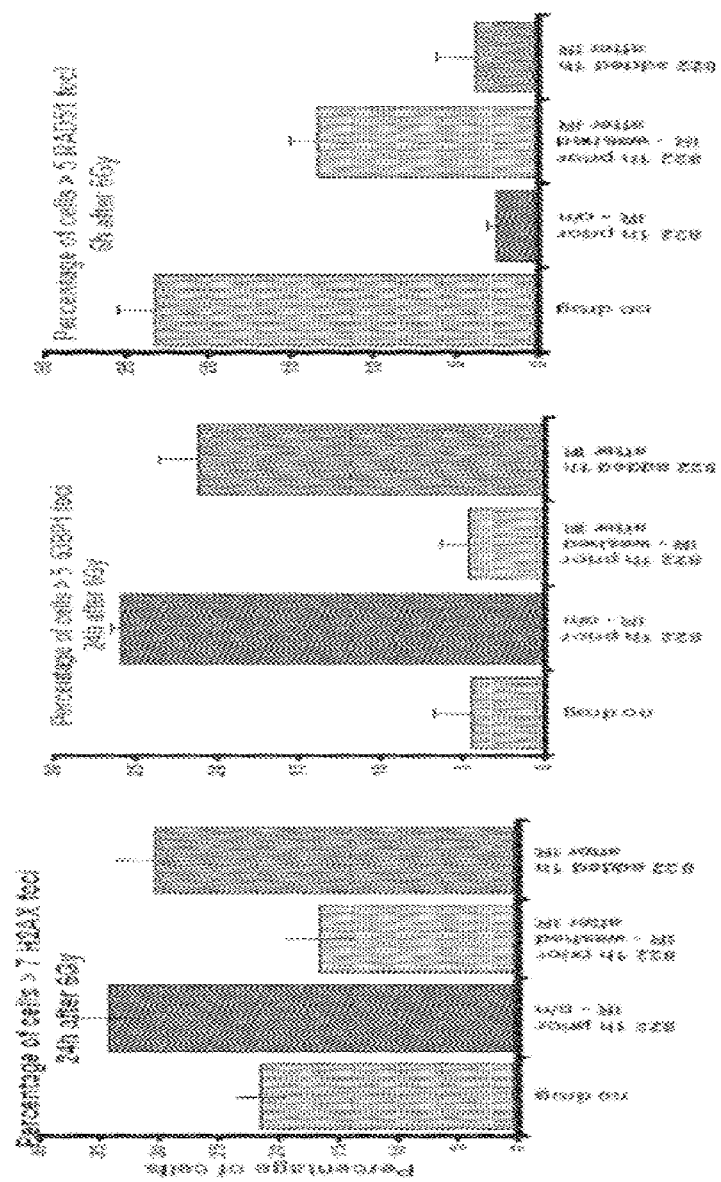
Figure 11:
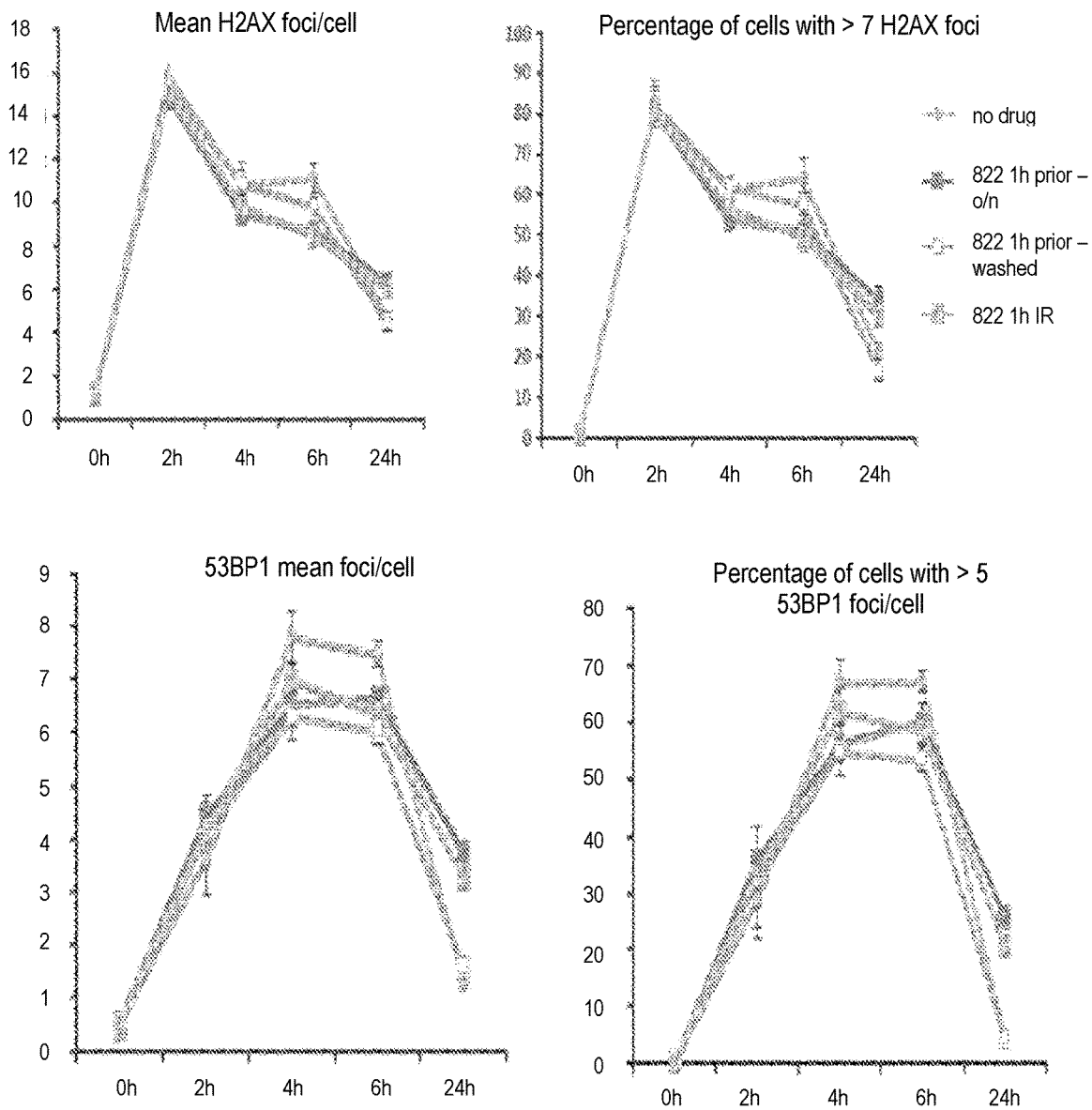
Figure 11:
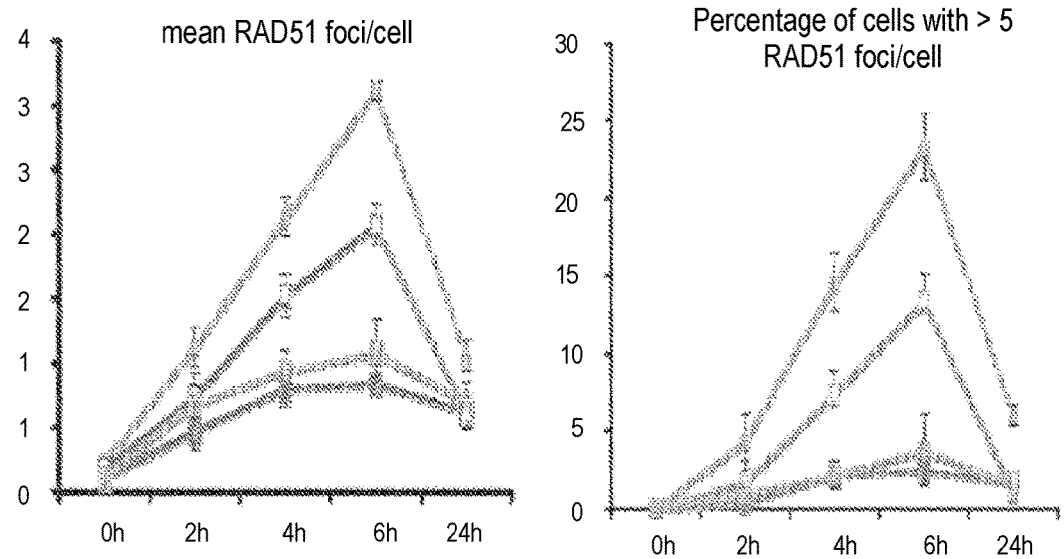

FIG. 11. DNA damage foci analysis after Compound 822 treatment and irradiation.

A) Assessment of gH2AX, 53BP1 foci at 24 h after IR at 6 Gy and of RAD51 foci at 6 h after IR. MiaPaca cells were treated with 80 nM Compound 822 1 h prior or 1 h post irradiation and drug was washed away at 5 min after or 1 h after IR. Cells were fixed after 6 h (for RAD51 foci) or 24 h (for gH2AX and 53BP1 foci). The percentage of cells containing more than a certain number of foci was quantitated.

B) Time course of DNA damage foci. Cells were treated as in A and fixed at the time points shown followed by staining for gH2AX, 53BP1 and RAD51 foci. Data is shown as the mean number of foci at a particular time point (upper panels) or the percentage of cells containing more than a certain number of foci (lower panels).

Figure 12:
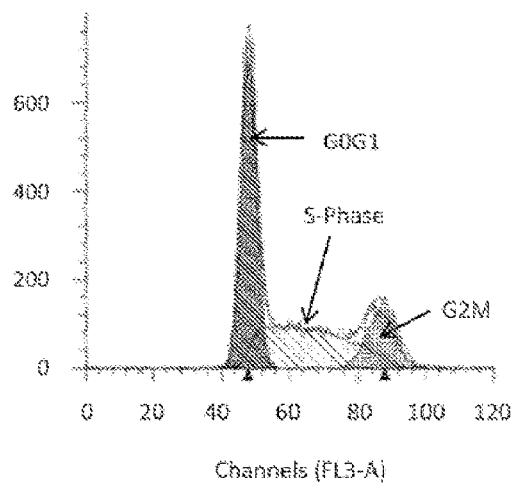
Figure 12:
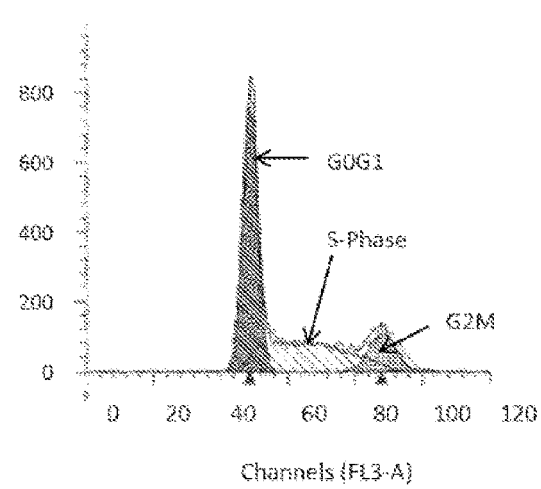
Figure 12:
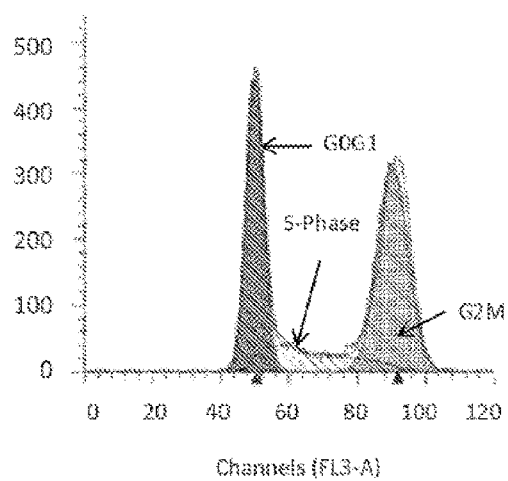
Figure 12:
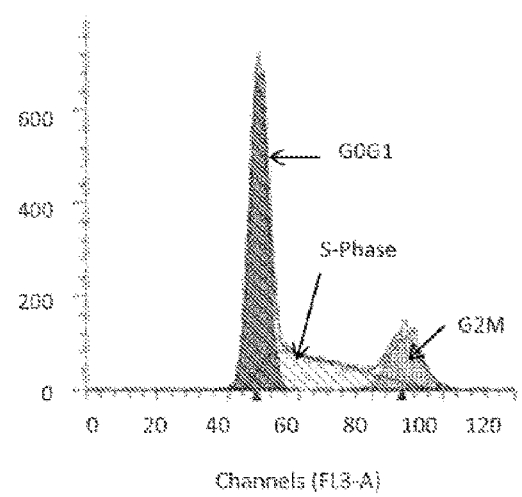
Figure 12:
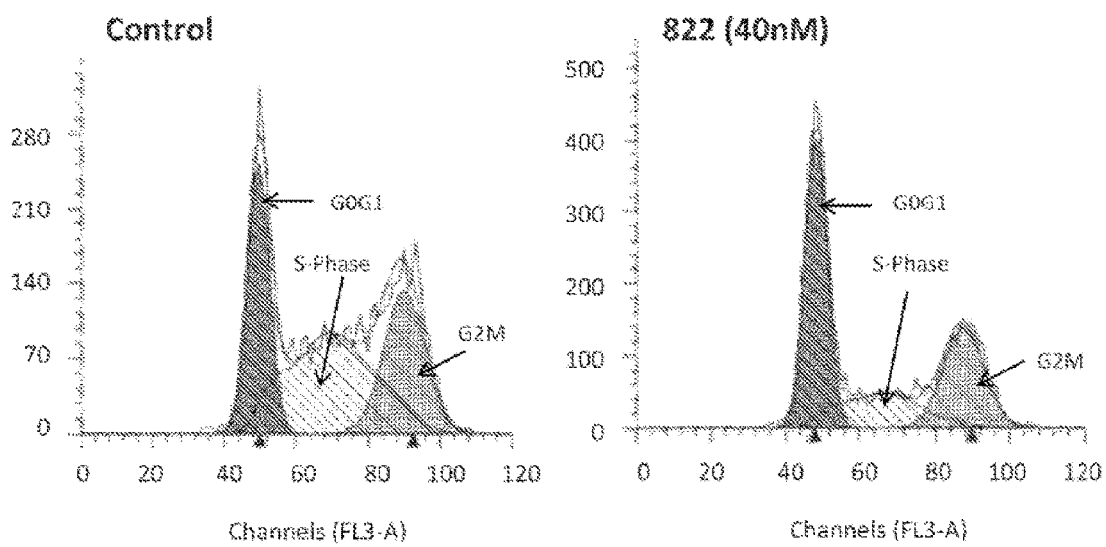
Figure 12:
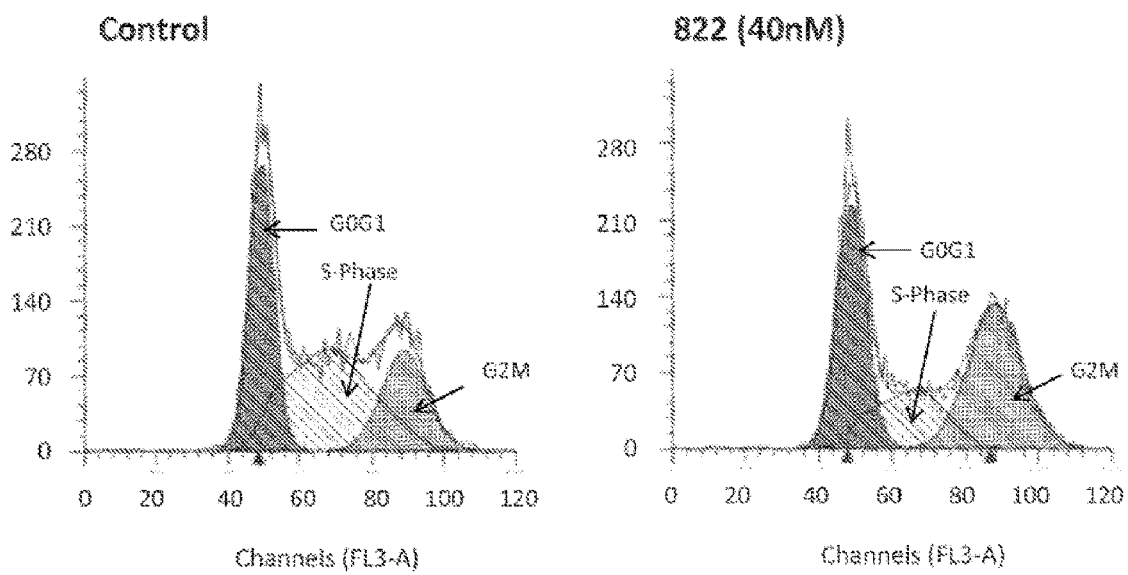
Figure 12:
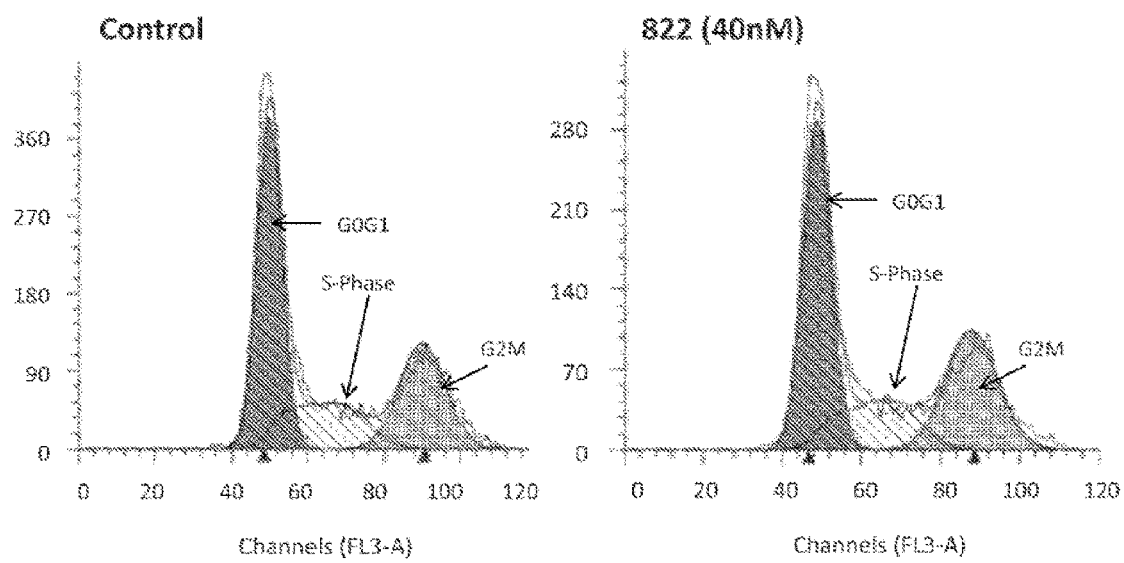
Figure 12:
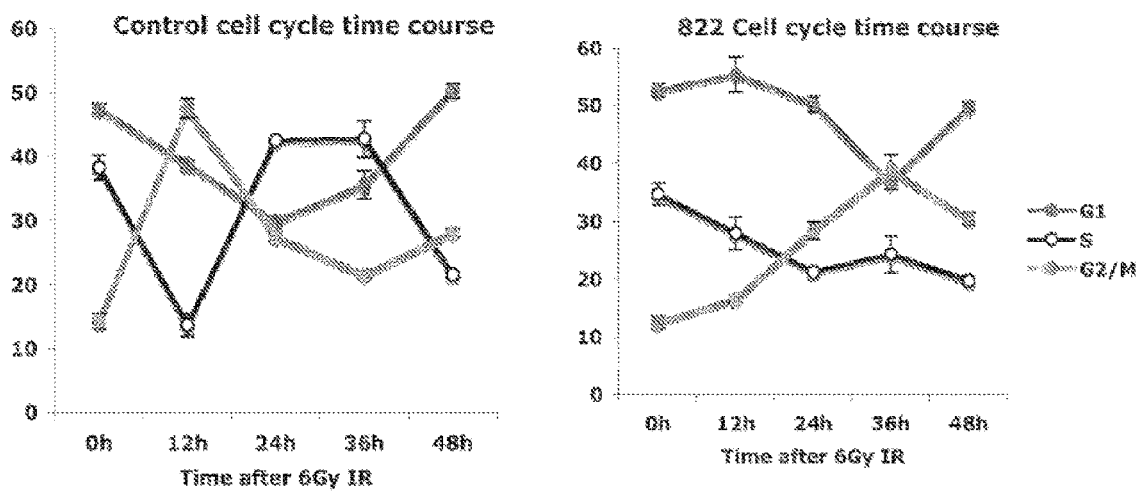

FIG. 12. Cell cycle analysis of Compound 822-treated cells after 6 Gy irradiation.

PSN1 cells were treated with 40 nM Compound 822 1 h prior to 6 Gy irradiation in triplicate wells. Cells were lifted and fixed at several time points after IR, stained with propidium iodide and analysed by flow cytometry.

A) Cell cycle histogram plots. Fitted peaks are coloured red for G1 phase, shaded for S-phase, and green for G2/M phase. One out of three wells is shown for each time point and treatment.

B) Average cell cycle percentages over time. Cell cycle percentage values were obtained from fitted histogram plots (n=3) and plotted for control-treated and Compound 822-treated cells.

Figure 13:
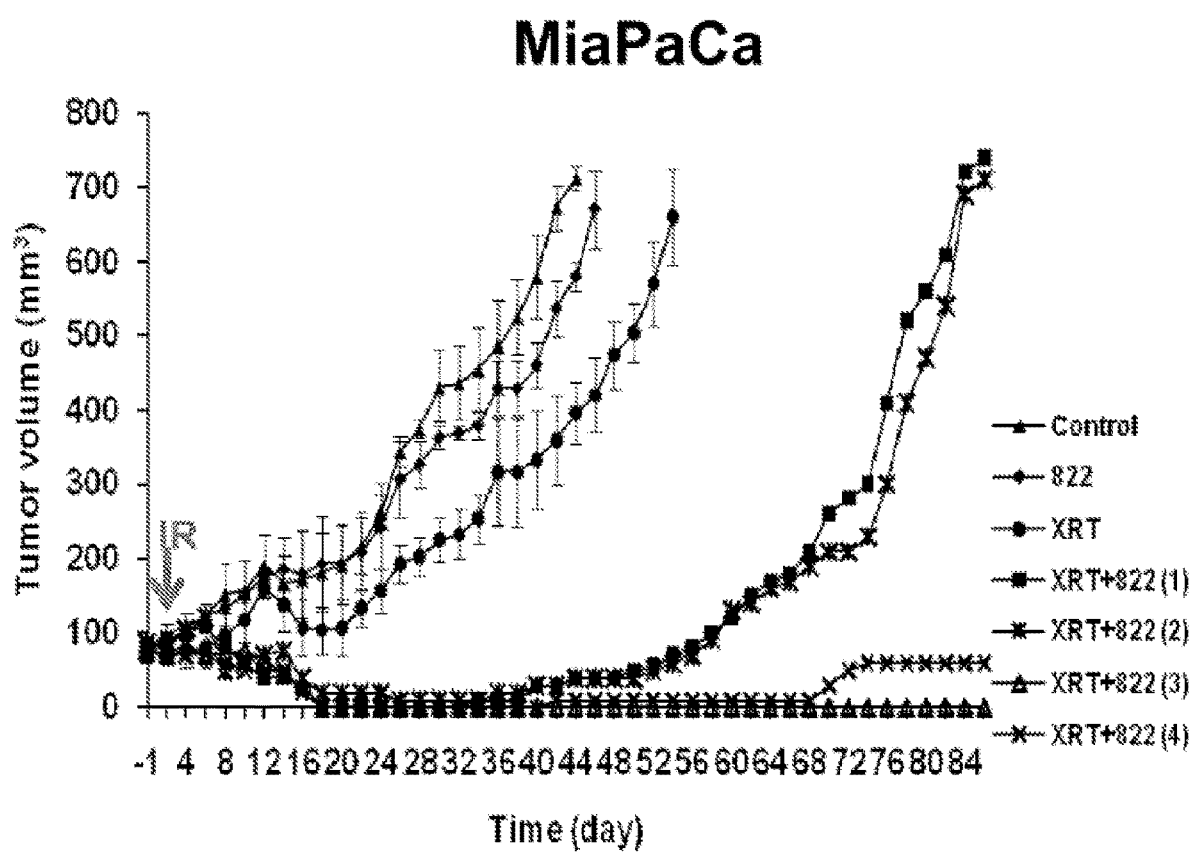

FIG. 13. MiaPaCa Tumor Volume over Time for Compound 822.

Figure 14:
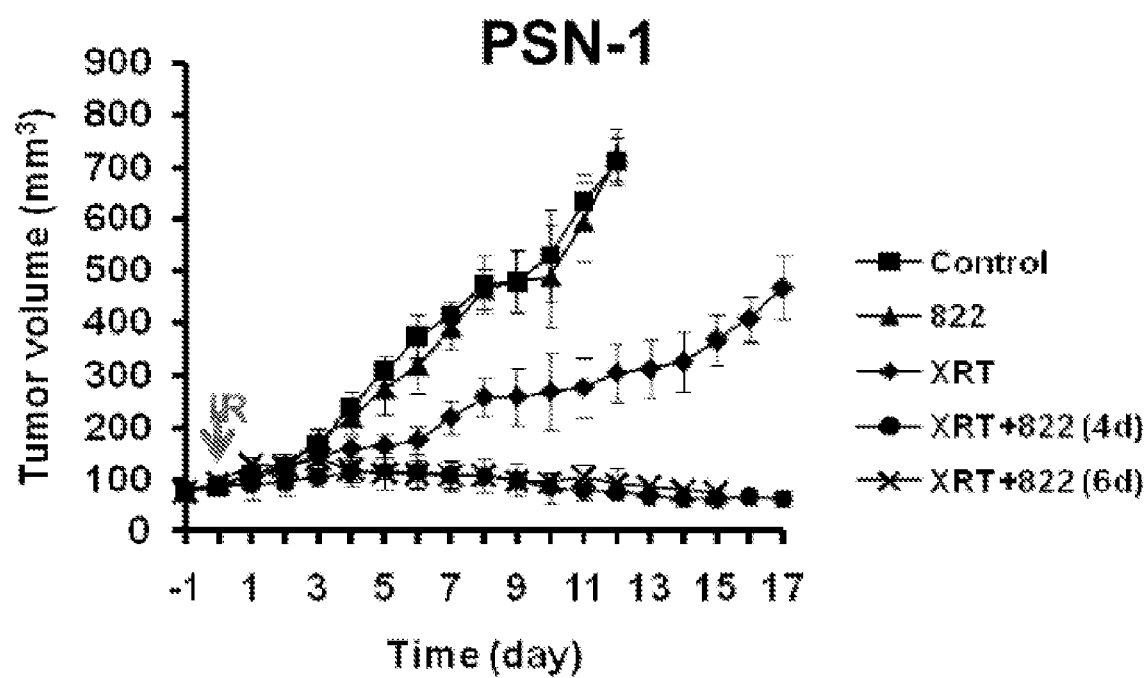
Figure 15:
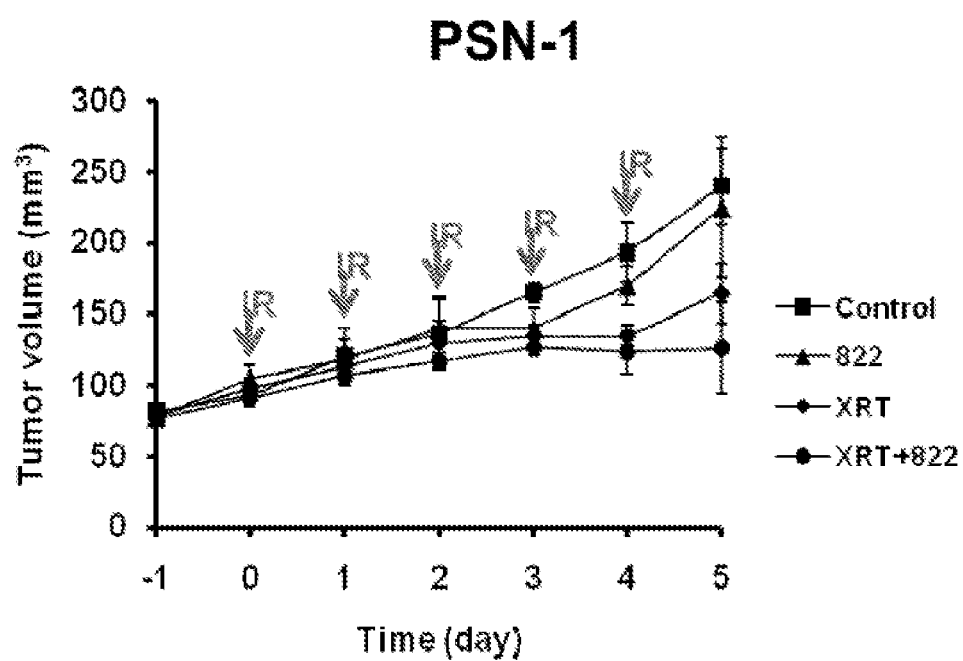

FIGS. 14 and 15. PSN-1 Tumor Volume over Time for Compound 822.

Figure 16:
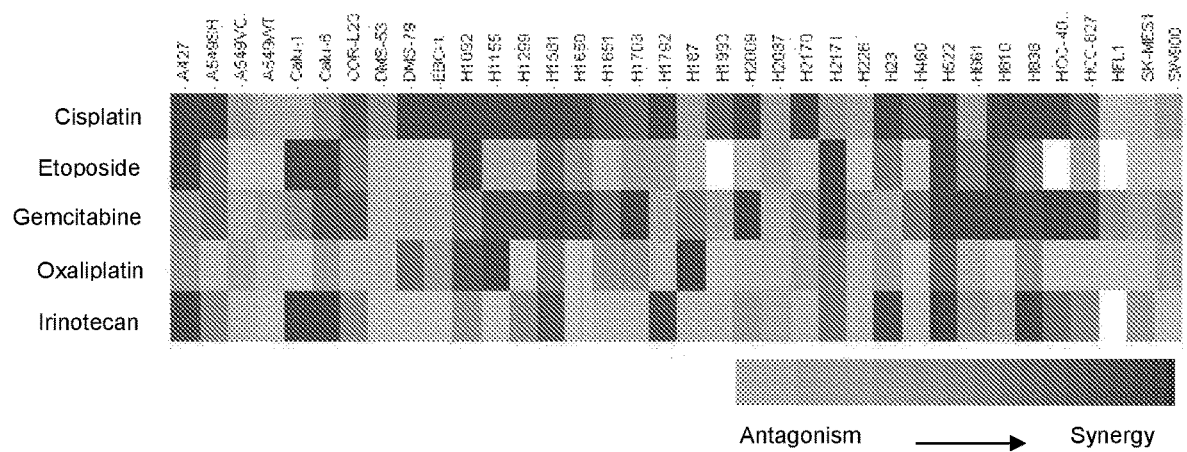
Figure 17:
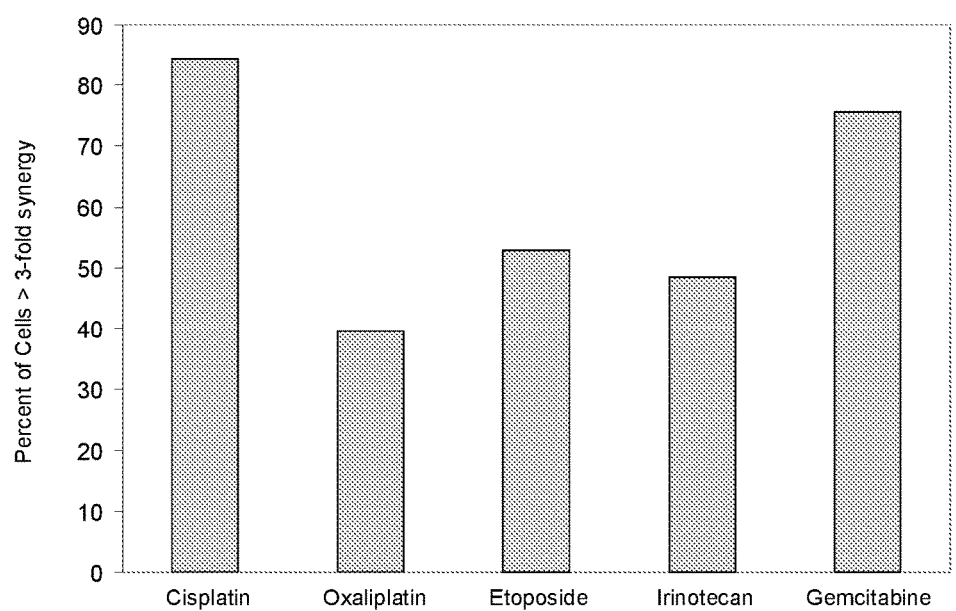
Figure 18:
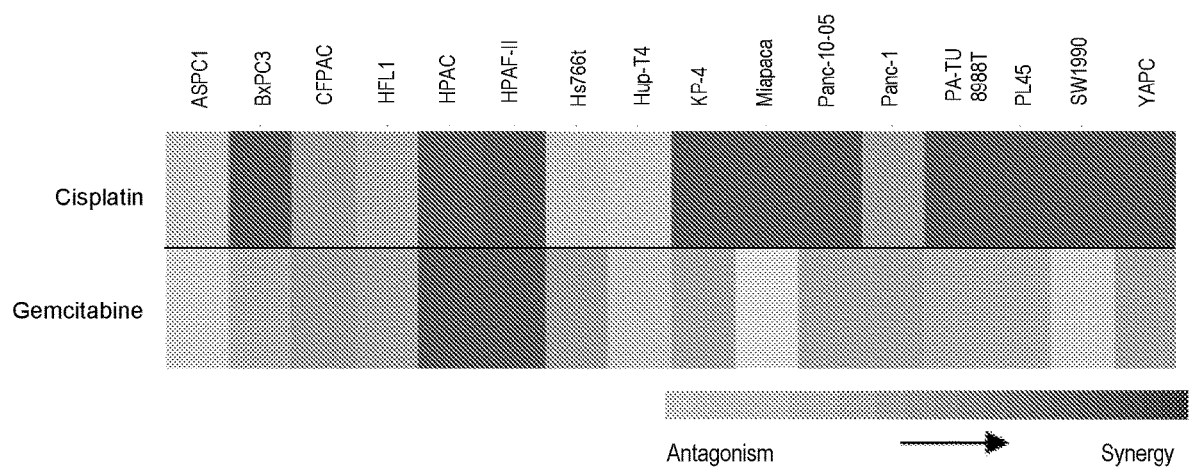
Figure 19:
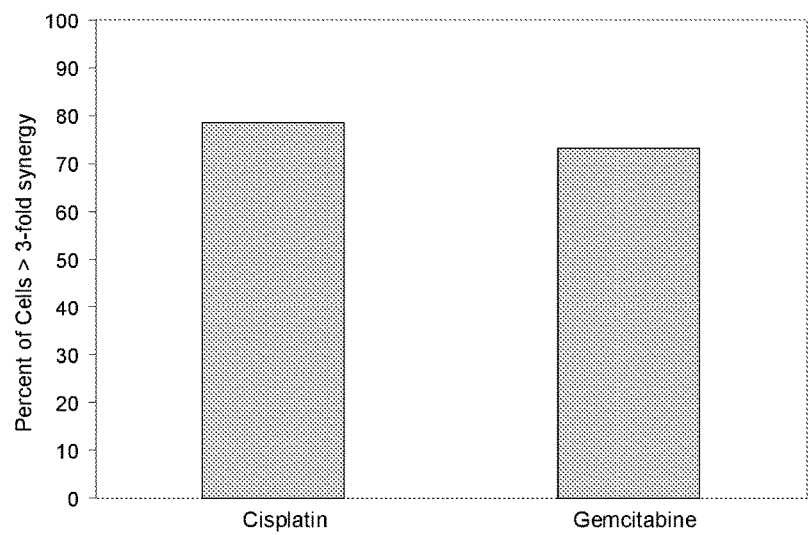

FIG. 16. Lung Cancer Cell Screen: VE-822 Synergizes with Chemotoxics Across a Panel of Lung Cancer Cell Lines in Lung Cell Viability Assay FIG. 17. Lung Cancer Cell Screen: VE-822 Exhibits Greater than 3-fold Synergy with Chemotoxics in Lung Cancer Cell Lines in a Cell Viability Assay FIG. 18. Pancreatic Cancer Cell Screen: VE-822 Synergizes with Cisplatin and Gemcitabine in Pancreatic Cancer Cell Lines in a Cell Viability Assay FIG. 19. Pancreatic Cancer Cell Screen: VE-822 Exhibits Greater than 3-fold Synergy with Chemotoxics in Pancreatic Cancer Cell Lines a Cell Viability Assay FIG. 20. Effect of VE-822 and cisplatin on tumor volume and body weight in a primary adenocarcinoma NSCLC xenograft in SCID mice.

Figure 21:
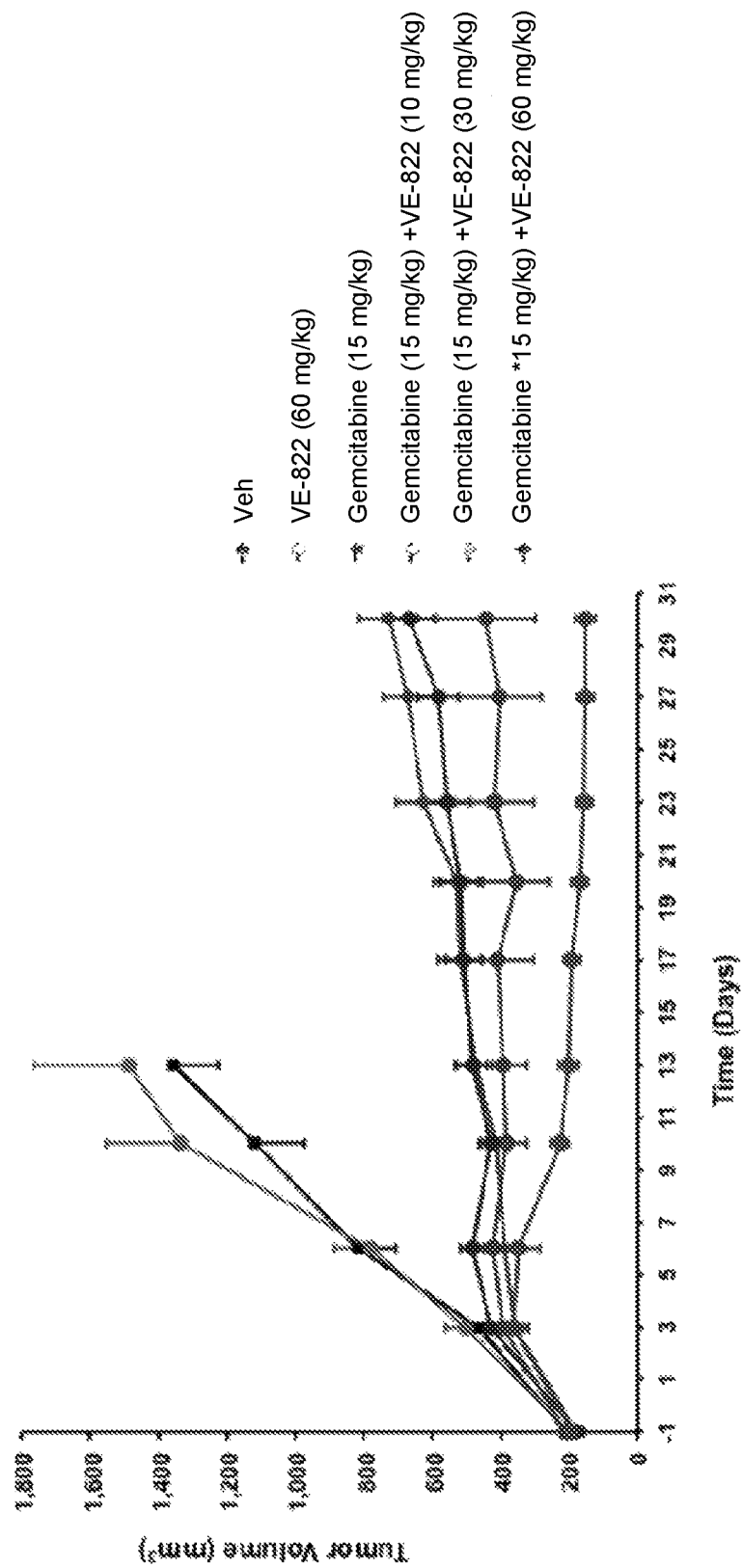

FIG. 21: Effect of VE-822 administered PO q2d at 10, 30 or 60 mg/kg in combination with gemcitabine (15 mg/kg IP q3d) on the tumor volume of mice bearing PSN1 pancreatic cancer xenografts.

DETAILED DESCRIPTION OF THE INVENTION

One aspect of this invention provides methods for treating pancreatic cancer in a patient by administering to the patient an ATR inhibitor in combination with another known pancreatic cancer treatment. One aspect of the invention includes administering the ATR inhibitor in combination with gemcitabine. In some embodiments, the pancreatic cancer comprises one of the following cell lines: PSN-1, MiaPaCa-2 or Panc-1. According to another aspect, the cancer comprises the primary tumor line Panc-M.

Another aspect of the invention provides methods for treating cancer (e.g., pancreatic or non-small cell lung) in a patient by administering to the patient an ATR inhibitor in combination with radiation therapy.

Another aspect of the invention provides methods for treating non-small cell lung cancer in a patient by administering to the patient an ATR inhibitor in combination with cisplatin or carboplatin, etoposide, and/or ionizing radiation. Applicants have demonstrated synergy of ATR inhibitors in combination with cisplatin, etoposide, gemcitabine, oxaliplatin and irinotecan in viability assays against a panel of 35 human lung cancer cell lines as well as demonstrated in vivo efficacy in a lung cancer mouse model in combination with cisplatin. This invention also relates to the use of ATR inhibitors in combination with cisplatin or carboplatin, etoposide, and/or ionizing radiation for treating non-small cell lung cancer.

Examples of ATR inhibitors are shown in Table 1 below:

TABLE 1

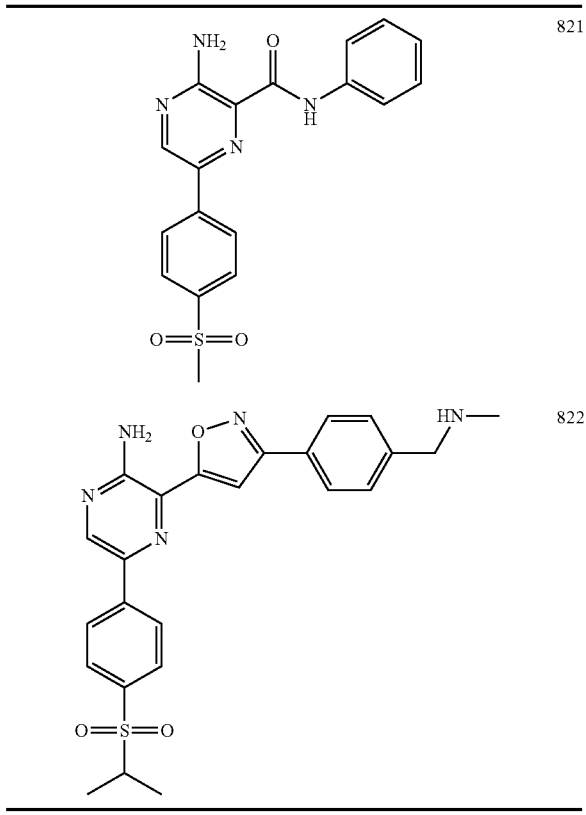

The terms referring to compounds 821 and 822 are interchangeable with VE-821 and VE-822, respectively.

Another aspect provides a method of treating pancreatic cancer by administering to pancreatic cancer cells an ATR inhibitor selected from a compound in Table 1 in combination with one or more cancer therapies. In some embodiments, the ATR inhibitor is combined with chemoradiation, chemotherapy, and/or radiation therapy. As would be understood by one of skill in the art, chemoradiation refers to a treatment regime that includes both chemotherapy (such as gemcitabine) and radiation. In some embodiments, the chemotherapy is gemcitabine.

Yet another aspect provides a method of increasing the sensitivity of pancreatic cancer cells to a cancer therapy selected from gemcitabine or radiation therapy by administering an ATR inhibitor selected from a compound in Table 1 in combination with the cancer therapy.

In some embodiments, the cancer therapy is gemcitabine. In other embodiments, the cancer therapy is radiation therapy. In yet another embodiment the cancer therapy is chemoradiation.

Another aspect provides a method of inhibiting phosphorylation of Chk1 (Ser 345) in a pancreatic cancer cell comprising administering an ATR inhibitor selected from a compound in Table 1 after treatment with gemcitabine (e.g., 100 nM) and/or radiation (e.g., 6 Gy) to a pancreatic cancer cell.

Another aspect provides method of radiosensitizing hypoxic PSN-1, MiaPaCa-2 or PancM tumor cells by administering an ATR inhibitor selected from a compound in Table 1 to the tumor cell in combination with radiation therapy.

Yet another aspect provides a method of sensitizing hypoxic PSN-1, MiaPaCa-2 or PancM tumor cells by administering an ATR inhibitor selected from a compound in Table 1 to the tumor cell in combination with gemcitabine.

Another aspect provides a method of sensitizing PSN-1 and MiaPaCa-2 tumor cells to chemoradiation by administering an ATR inhibitor selected from a compound in Table 1 to the tumor cells in combination with chemoradiation.

Another aspect provides a method of disrupting damage-induced cell cycle checkpoints by administering an ATR inhibitor selected from a compound in Table 1 in combination with radiation therapy to a pancreatic cancer cell.

Another aspect provides a method of inhibiting repair of DNA damage by homologous recombination in a pancreatic cancer cell by administering an ATR inhibitor selected from a compound in Table 1 in combination with one or more of the following treatments: chemoradiation, chemotherapy, and radiation therapy.

In some embodiments, the chemotherapy is gemcitabine.

Another aspect provides a method of inhibiting repair of DNA damage by homologous recombination in a pancreatic cancer cell by administering an ATR inhibitor selected from a compound in Table 1 in combination with gemcitabine and radiation therapy.

In some embodiments, the pancreatic cancer cells are derived from a pancreatic cell line selected from PSN-1, MiaPaCa-2 or Panc-1.

In other embodiments, the pancreatic cancer cells are in a cancer patient. In other embodiments, the cancer cells are part of a tumor.

Another embodiment provides methods for treating non-small cell lung cancer in a patient by administering to the patient an ATR inhibitor in combination with other known non-small cell lung cancer treatments. One aspect of the invention includes administering to a patient an ATR inhibitor in combination with cisplatin or carboplatin, etoposide, and/or ionizing radiation.

Another aspect provides a method of treating non-small cell lung cancer by administering to a patient an ATR inhibitor selected from a compound in Table 1 in combination with one or more cancer therapies. In some embodiments, the ATR inhibitor is combined with chemoradiation, chemotherapy, and/or radiation therapy. As would be understood by one of skill in the art, chemoradiation refers to a treatment regime that includes both chemotherapy (such as cisplatin, carboplatin, or etoposide) and radiation. In some embodiments, the chemotherapy comprises Cisplatin or carboplatin, and etoposide.

Yet another aspect provides a method of increasing the sensitivity of non-small cell lung cancer cells to a cancer therapy selected from cisplatin or carboplatin, etoposide, and ionizing radiation by administering to a patient an ATR inhibitor selected from a compound in Table 1 in combination with one or more cancer therapy.

In some embodiments, the cancer therapy is cisplatin or carboplatin. In other embodiments, the cancer therapy is radiation therapy. In yet another embodiment the cancer therapy is etoposide.

In some embodiments, the cancer therapy is a combination of cisplatin or carboplatin, etoposide, and ionizing radiation. In some embodiments the cancer therapy is cisplatin or carboplatin and etoposide. In other embodiments the cancer therapy is cisplatin or carboplatin and etoposide and ionizing radiation. In yet other embodiments the cancer therapy is cisplatin or carboplatin and ionizing radiation.

Another aspect provides a method of inhibiting phosphorylation of Chk1 (Ser 345) in a non-small cell lung cancer cell comprising administering to a patient an ATR inhibitor selected from a compound in Table 1. In some embodiments, the ATR inhibitor is administered in combination with gemcitabine (e.g., 100 nM), cisplatin or carboplatin, etoposide, ionizing radiation or radiation (e.g., 6 Gy) to a non-small cell lung cancer cell.

In other embodiments, the non-small cell lung cancer cells are in a cancer patient.

In some embodiments, the ATR inhibitor is

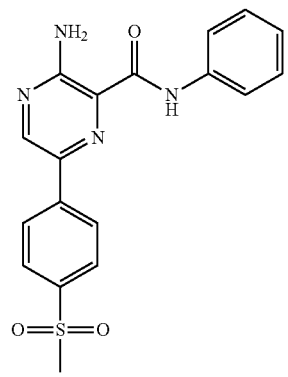 [SMILES: CS(=O)(=O)c1ccc(-c2cnc(N)c(C(=O)Nc3ccccc3)n2)cc1]

821

In other embodiments, the ATR inhibitor is

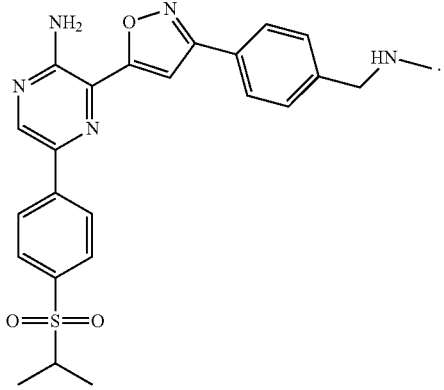

Uses

Another aspect provides use of an ATR inhibitor selected from a compound in Table 1 in combination with gemcitabine and radiation therapy for treating pancreatic cancer.

Another aspect provides use of an ATR inhibitor selected from a compound in Table 1 in combination with cisplatin or carboplatin, etoposide, and ionizing radiation for treating non-small cell lung cancer.

In some embodiments, the ATR inhibitor is Compound VE-821. In other embodiments, the ATR inhibitor is Compound VE-822.

Manufacture of Medicaments

Another aspect provides use of an ATR inhibitor selected from a compound in Table 1 in combination with gemcitabine and radiation therapy for the manufacture of a medicament for treating pancreatic cancer.

Another aspect provides use of an ATR inhibitor selected from a compound in Table 1 in combination with cisplatin or carboplatin, etoposide, and ionizing radiation for the manufacture of a medicament for treating non-small cell lung cancer.

In some embodiments, the ATR inhibitor is Compound VE-821. In other embodiments, the ATR inhibitor is Compound VE-822.

EXAMPLES

The examples are for the purpose of illustration only and are not to be construed as limiting the scope of the invention in any way.

Cell Viability Assays

MiaPaCa-2, PSN-1, Panc1 and MRCS cells (5×104) were plated in 96-well plates and after 4 h treated with increasing concentrations of VE-821 at 1 h before irradiation with a single dose of 6 Gy. Medium was replaced 96 h post-irradiation at which point viability was measured using the using the Alamar Blue assay (Resazurin substrate, SIGMA). Cells were allowed to proliferate and cell viability was again analyzed at day 8 for the different treatment conditions. Cell viability and surviving fraction were normalized to the untreated (control) group.

Clonogenic Survival Assay

Logarithmically growing cells were plated in triplicate in 6-well tissue culture dishes under oxic (21% $O_2$) or hypoxic conditions (0.5% $O_2$) using an InVivo2 300 chamber (Ruskinn Technology, UK). Cells were incubated for 6 hours before irradiation under oxia or hypoxia using tightly sealed chambers. The target $O_2$ level was achieved within 6 h of gassing and maintained during irradiation, as confirmed by an OxyLite oxygen probe (Oxford Optronix). Cells irradiated under hypoxia were exposed to normoxia at 1 h post-irradiation. As standard, VE-821 (1 μM) was added 1 h prior to irradiation (6 Gy) and was washed away 72 h after irradiation. For the chemotherapy experiments, cells were initially exposed to increasing concentrations of gemcitabine (5, 10 and 20 nM) for 24 h before addition of the VE-821 (1 μM) for another 72 h. The effect of triple combination of irradiation with VE-821 and gemcitabine was examined as well. Cells were incubated for 10-21 days until colonies were stained with 0.5% crystal violet and counted in a CellCount automated colony counter (Oxford Optronix). Clonogenic survival was calculated and data were fitted in the GraphPad Prism 4.0 (GraphPad Software, CA).

Western Blot

MiaPaCa-2 and PSN-1 cells were exposed to gemcitabine and/or 1 μM VE-821 drug 1 h prior to irradiation with a single dose of 6 Gy. Cells were lysed in RIPA buffer 2 h post-irradiation and subjected to SDS-PAGE electrophoresis and immunoblotting. Chemoluminescence (SuperSignal, Millipore) and film exposure was used to detect antibody binding. Exposed film was digitized and figures were assembled using Microsoft PowerPoint.

Nuclear Foci Analysis

Cells growing in 96-well plates were treated with 1 μM VE-821 drug 1 h prior to 6 Gy irradiation and fixed in 3% formaldehyde at multiple time points. Cells were subsequently pearmeabalised and blocked in PBS with 0.1% Triton 1% BSA (w/v). Cells were incubated with primary antibody overnight at 4° C. and after a PBS wash incubated with fluorescently labeled secondary antibody followed gy a PBS wash and nuclear staining with DAPI. Images were acquired and foci quantitated using an IN Cell Analyzer 1000 automated epifluorescence microscope and analysis software (GE Healthcare, Cahlfont St. Giles, UK)

Cell Cycle Analysis

Cells growing in 6-well dishes were treated with 1 μM VE-821 drug 1 h prior to 6 Gy irradiation. Cells were incubated for 6 h before irradiation under oxia (21% O2) or hypoxia (0.5% O2) using tightly sealed chambers. At multiple time points, cells were lifted in trypsin and fixed in 70% ethanol and stored at 4° C. Cells were incubated with propidium iodide (50 μg/ml in PBS containing 200 μg/ml RNAse) for 1 h at room temperature and analysed by flow cytometry (FACSort, Becton Dickinson). Cell cycle phase was quantitated using ModFit Cell Cycle Analysis software.

Cell Seeding and Compound Addition for Lung Cancer Cell Screen

All cell lines were seeded in 30 μl of tissue culture medium containing 10% FBS into 384-well opaque-bottom assay plates. The seeding density was based on the logarithmic growth rate of each cell line. After 24 hours, compound stock solutions were added to each well to afford a matrix consisting of 5 concentrations for VE-822 and 6 concentrations for chemotoxics. Each well contains either, agent alone or a combination of both agents. The final concentration range for VE-822 was 25 nM-2 μM. The concentration ranges for the chemotoxics were as follows: Etoposide, 10 nM-10 μM; Gemcitabine, 0.16 nM-160 nM; Cisplatin, 20 nM-20 μM; Oxaliplatin, 40 nM-40 μM; Irinotecan (SN-38), 0.12 nM-120 nM. The cells were then incubated for 96 hours at 37° C. in an atmosphere of 5% $CO_2$ and 95% humidity.

Cell Seeding and Compound Addition for the Pancreatic Cancer Cell Screen

All cell lines were seeded in 30 μl of tissue culture medium containing 10% FBS into 384-well opaque-bottom plates. The seeding density was based on the logarithmic growth rate of each cell line. After 24 hours, compound stock solutions were added to each well to afford a matrix consisting of 9 concentrations for VE-822 and 7 concentrations for Gemcitabine and Cisplatin. Each well contains either, agent alone or a combination of both agents. The final concentration ranges were as follows: VE-822, 0.3 nM-2 μM; Gemcitabine, 0.3 nM-0.22 μM; Cisplatin, 30 nM-20 μM. The cells were then incubated for 96 hours at 37° C. in an atmosphere of 5% $CO_2$ and 95% humidity.

Cell Viability Assay

This assay measures the number of viable cells in a culture based on the quantitation of ATP, which is present in metabolically active cells.

CellTiter-Glo Reagent (Promega, Madison, Wis., USA) was prepared according to the manufacturer's instructions and added 96 hours after compound addition (25 μl/well) to measure cell viability. Luminescence signal was measured with the PHERAStarFS (BMG Labtech, Cary, N.C., USA) automated plate reader. All cell lines were screened in duplicate.

Raw luminescence CellTiter-Glo (CTG) values were normalized to the mean CTG value for the negative control DMSO-treated samples on each assay plate. $IC_{50}$ values for chemotoxic alone were calculated using DMSO-normalized cell survival values for the samples treated with chemotoxic compound alone. To determine fraction of cell survival in the presence of VE-822, raw CTG values were normalized to the mean CTG value for the samples exposed to the same concentration of VE-822 in the absence of the chemotoxic compound. VE-822-treated chemotoxic $IC_{50}$ values were calculated using VE-822-normalized cell survival values for all samples treated with the chemotoxic at a given concentration of VE-822. A 3× or greater reduction in $IC_{50}$ was used to identify strongly synergistic effects between VE-822 and chemotoxics.

Primary Adenocarcinoma NSCLC Xenograft Model

Tumor tissue was excised from a patient with a poorly differentiated adenocarcinoma. This tumor tissue was implanted subcutaneously in the flank of a SCID mouse and passaged twice before compound testing. For compound testing passage-two tumor tissue was implanted subcutaneously in the flank of SCID mice and tumors grown to a volume of about 200 $mm^3$ Cisplatin was dosed alone at either 1 or 3 mg/kg ip, once per week (ip, q7d, on day 2 of each week) for two weeks. VE-822 was dosed as a solution alone at 60 mg/kg po on 4 consecutive days per weekly cycle (qd4, dosed on days 1, 2, 3 and 4 each week). Two combination groups received cisplatin at 1 or 3 mg/kg plus VE-822 at 60 mg/kg po on the same schedule as the single agent group. A control group received vehicle alone (10% Vitamin E TPGS in water, po qd4). All drug treatment was stopped on Day 28. Vehicle, cisplatin (1 mg/kg) and VE-822 (60 mg/kg) groups were sacrificed and the remainder monitored for a further 40 days to assess tumor re-growth.

PSN1 Pancreatic Cancer Xenograft Model

PSN1 cells ($1\times10^6$ cells per mouse) were implanted as a mixture in Matrigel (100 μl per mouse) into the flank of female nude MF1 mice and grown to a volume of about 200 $mm^3$ prior to compound administration. Gemcitabine was dosed alone at 15 mg/kg ip, once every three days (ip, q3d) in 0.5% methylcellulose in water for a maximum of 10 cycles. VE-822 was dosed, as a suspension in 0.5% methylcellulose in water, alone at either 10, 30 or 60 mg/kg po every other day for 28 days (po q2d). Three combination groups received gemcitabine at 15 mg/kg plus VE-822 either at 10, 30 or at 60 mg/kg po on the same schedule as the single agent groups. A control group received vehicle alone (0.5% methylcellulose ip q3d). All drug treatment was stopped on Day 30. Vehicle and VE-822 groups were sacrificed on day 13 due to excessive tumor volumes.

Results

Figure 1:
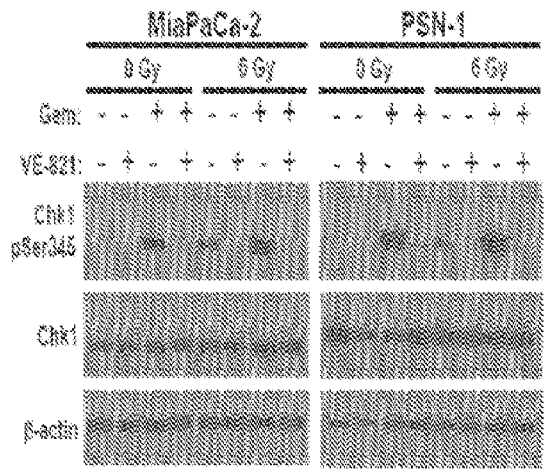
FIG. 1. VE-821 radiosensitises pancreatic tumour cells.
a) Western Blot Analysis of Chk1 Inhibition.
Cells were treated with 100 nM gemcitabine for 1 h, 1 µM VE-821 was added 1 h later and cells were irradiated (6 Gy) 1 h after that. Drugs were left for the duration of the experiment and cells were lysed at 2 h post-irradiation and subjected to Western blot analysis.
B) VE-821 Radiosensitizes Pancreatic Tumour Cells but not Normal Fibroblasts.
PSN-1, Panc-1, MiaPaCa-2 pancreatic cancer cell lines and MRCS fibroblasts were treated with increasing concentrations of VE-821 for 96 h combined with or without 4 Gy radiation at 1 h after VE-821 addition. Cell viability was measured after 8 days and shown as normalized to DMSO-treated cells.
C) Scheduling of VE-821 Affects Radiosensitivity.
PSN-1 cells were plated as single cells, treated with 1 µM VE-821 at different time points in relation to 4 Gy irradiation and assessed for colony formation after 10 days. The survival fraction at 4 Gy for each of the treatment schedules was determined by taking into account the relevant plating efficiency of unirradiated cells.
D) Clonogenic Survival of Cells Pancreatic Cancer Cells in Response to ATR Inhibition.
Cells were treated with 1 µM VE-821 4 h after plating and 1 h prior to irradiation. Drug was removed after 72 h and colony-forming ability was assessed after 10 to 21 days. (n=3). *, $P<0.05$; **, $P<0.01$ over DMSO-treated control.
Figure 1:
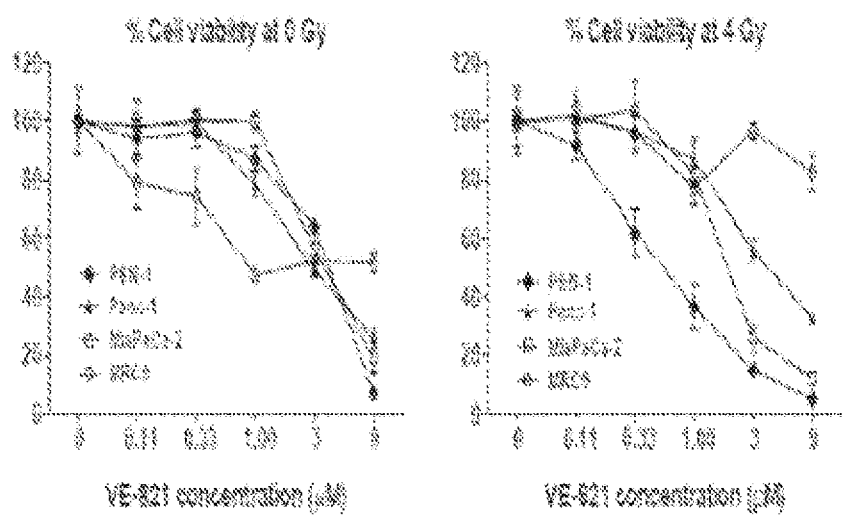
Figure 1:
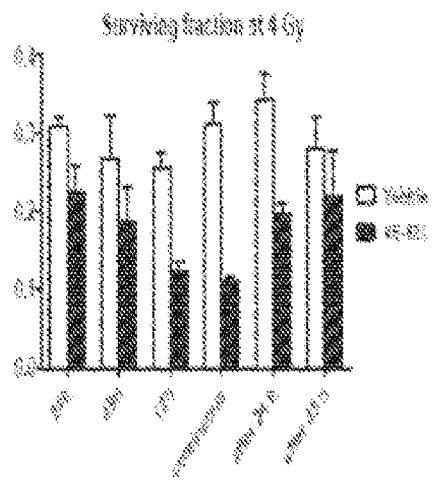
Figure 1:
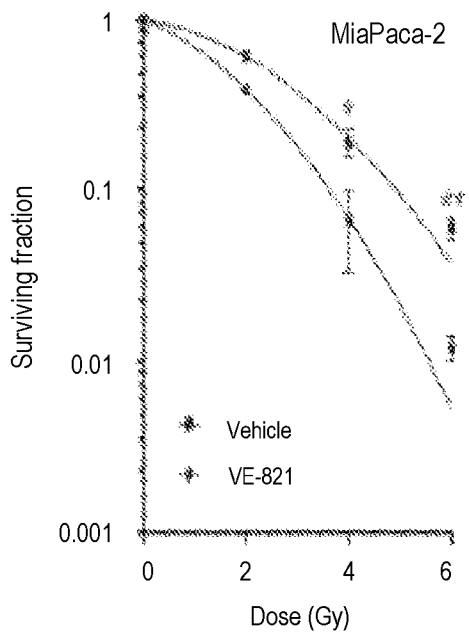
Figure 1:
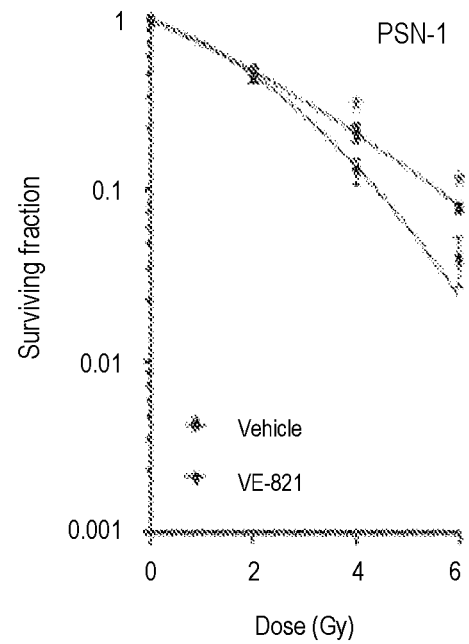
Figure 1:
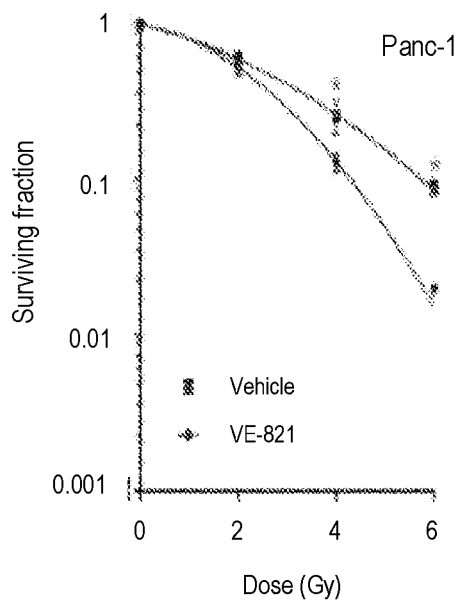
Figure 1:
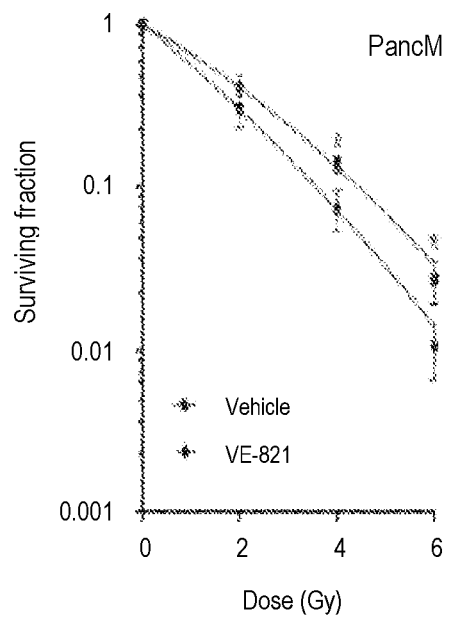

Compounds VE-821 and VE-822 Sensitize Pancreatic Cancer Cells to Radiation Therapy Compound VE-821 inhibits phosphorylation of Chk1 (Ser 345) after treatment with gemcitabine (100 nM), radiation (6 Gy) or both (see FIG. 1, panel A). Compound VE-821 radiosensitises pancreatic tumour cells but not normal cells. When cells were irradiated in the presence of Compound VE-821, a decrease in surviving fraction was observed and this radiosensitising effect increased as the drug incubation time after irradiation was extended (see FIG. 1, panel C).

Figure 2:
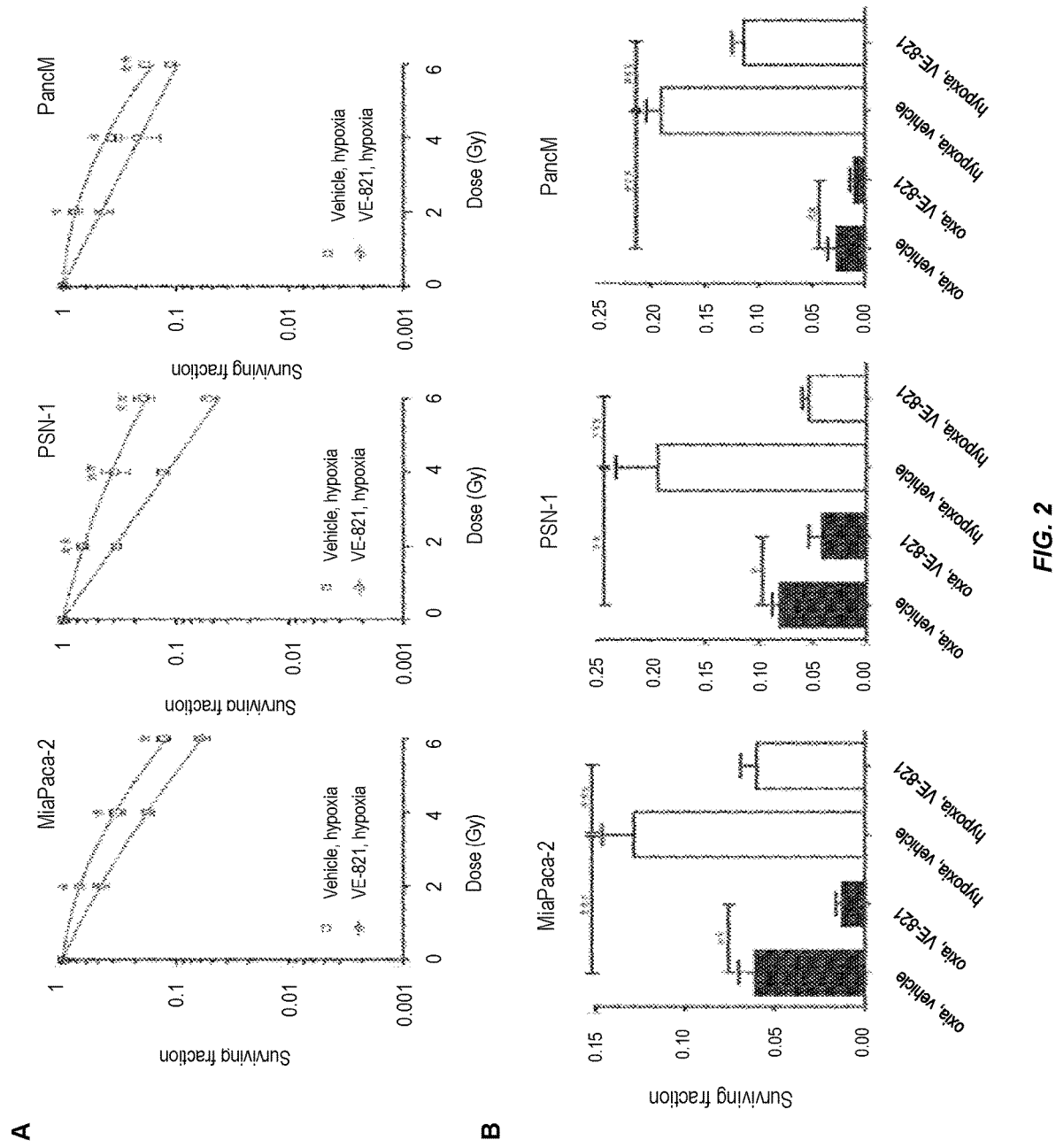
FIG. 2. VE-821 radiosensitises pancreatic tumour cells under hypoxic conditions.
A) clonogenic survival curves of cells treated with 1 µM VE-821 and irradiation under hypoxic conditions. Plated cells were transferred to hypoxia (0.5% $O_2$) and acclimatised for 6 h. VE-821 (1 µM) was then added at 1 h prior to irradiation and left for 72 h upon which the medium was replaced. Cells were transferred to normoxia at 1 h post-irradiation.
B) clonogenic survival of cells after irradiation with 6 Gy and treatment with 1 µM VE-821 in oxic and hypoxic (0.5% $O_2$) conditions, as described above and in FIG. 1 (n=3). *, $P<0.05$; , $P<0.01$; *, $P<0.001$ over DMSO-treated control.
Figure 3:
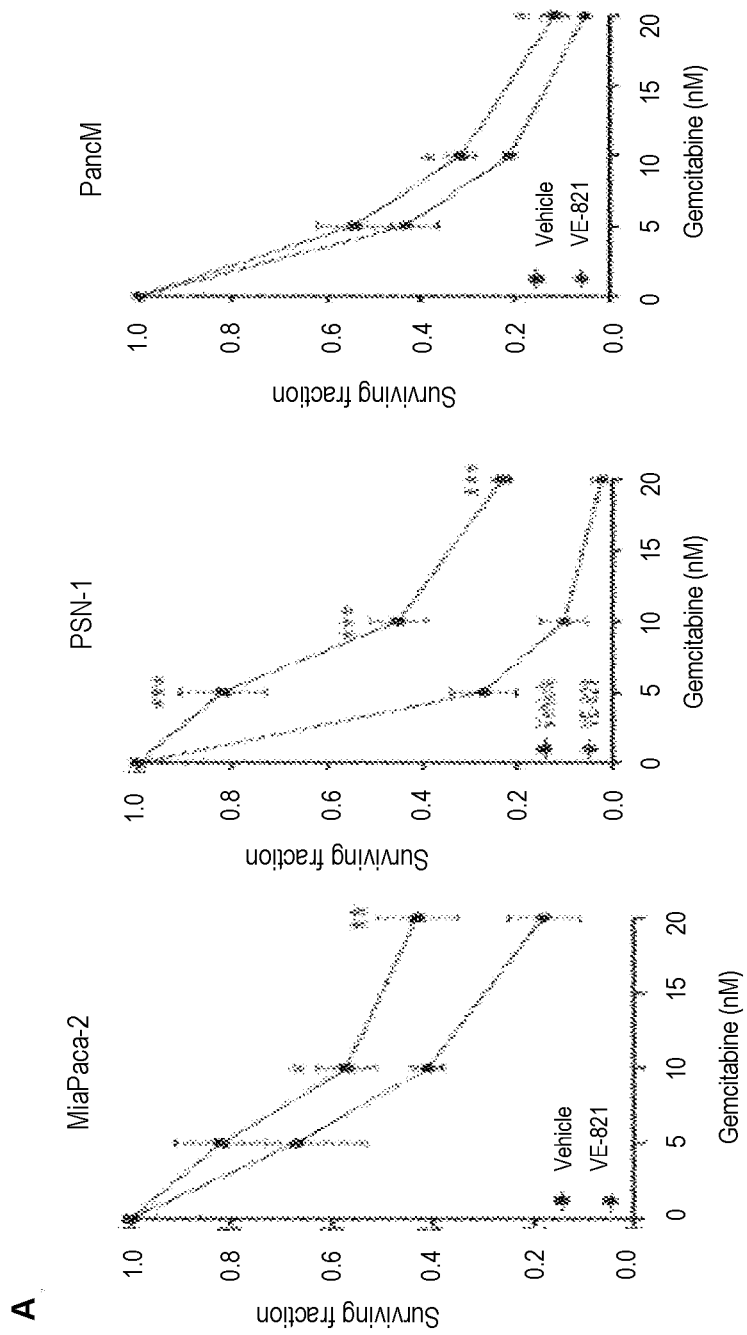
FIG. 3. VE-821 sensitises pancreatic cancer cells to gemcitabine treatment.
A) clonogenic survival of cells treated with gemcitabine and 1 µM VE-821. Cells were treated with increasing concentrations of gemcitabine for 24 h followed by 72 h treatment of 1 µM VE-821. Colony forming ability was assessed after 10 to 21 days.
B) clonogenic survival of cells treated with gemcitabine in hypoxia. Plated cells were transferred to hypoxia (0.5% $O_2$) and acclimatised for 6 h. Cells were then treated with increasing concentrations of gemcitabine for 24 h followed by 72 h treatment of 1 µM VE-821. Hypoxic cells were transferred to normoxia 1 h after VE-821 addition.
C) clonogenic survival after treatment with 20 nM gemcitabine and VE-821 in oxic and hypoxic (0.5% $O_2$) conditions, as described above.
D) clonogenic survival of cells treated with gemcitabine and irradiation. PSN-1 and MiaPaCa-2 cells were treated with 5 nM or 10 nM gemcitabine, respectively, for 24 h, medium was then replaced and 1 µM VE-821 was added from 1 h prior to 72 h post 4 Gy irradiation. Colony forming ability was assessed after 10 to 21 days (n=3). *, $P<0.05$; , $P<0.01$; *, $P<0.001$ over DMSO-treated control.
Figure 3:
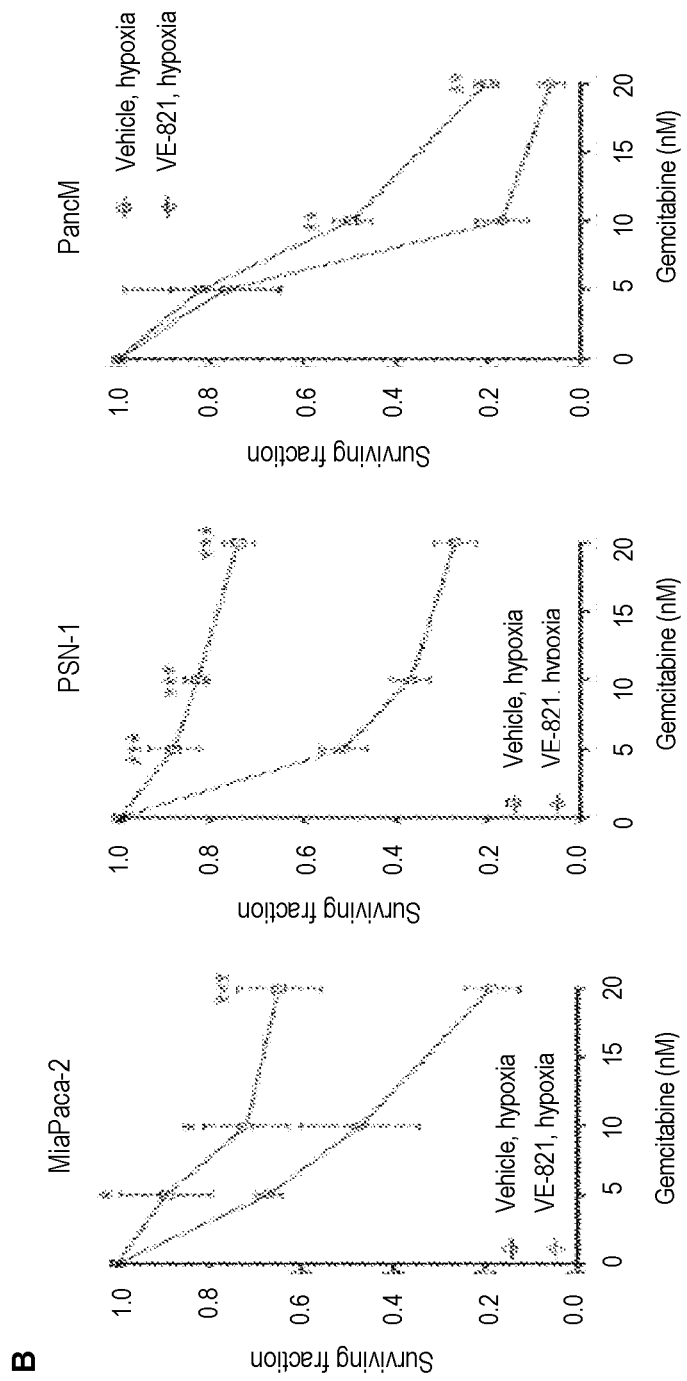
Figure 3:
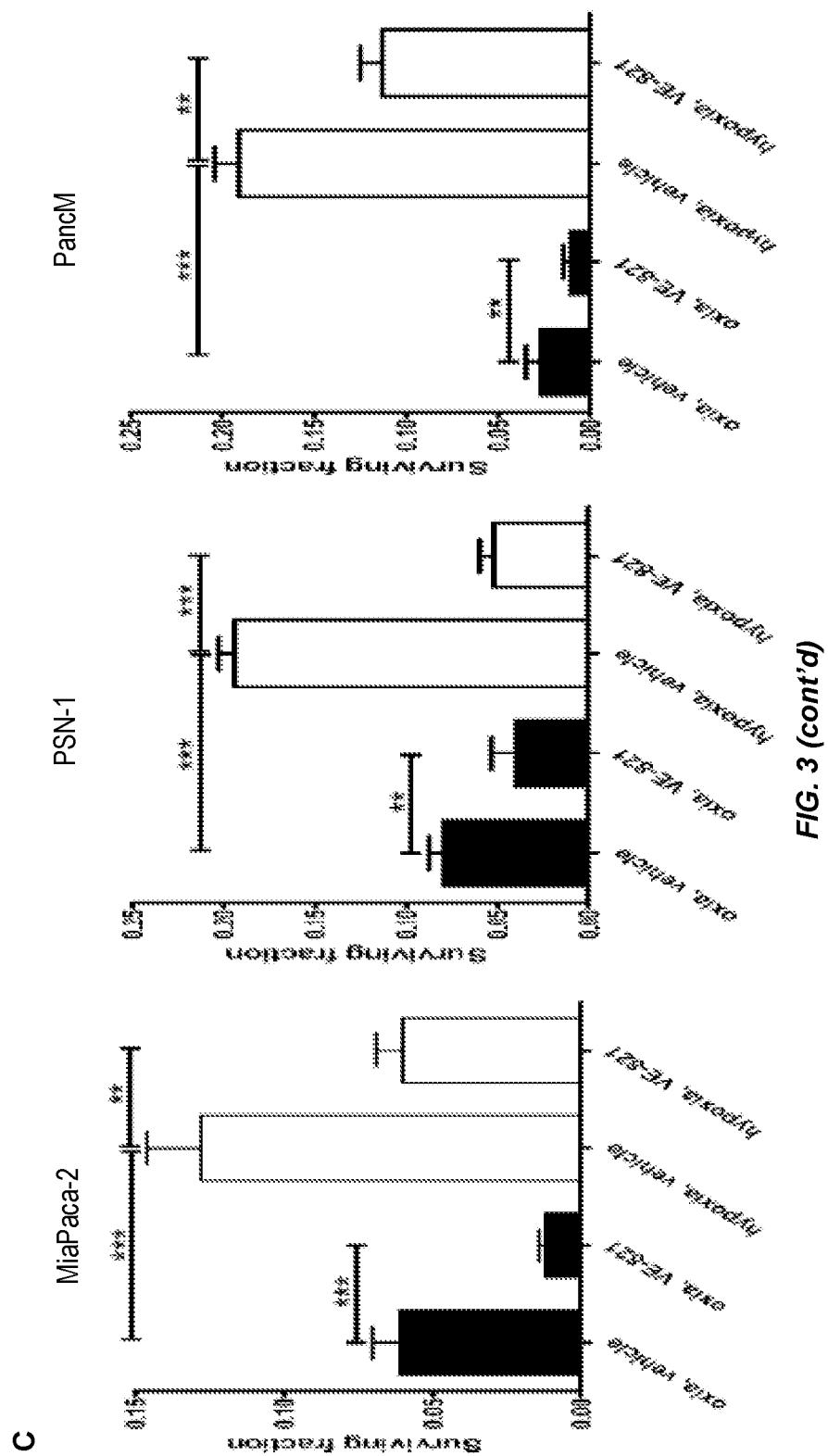
Figure 3:
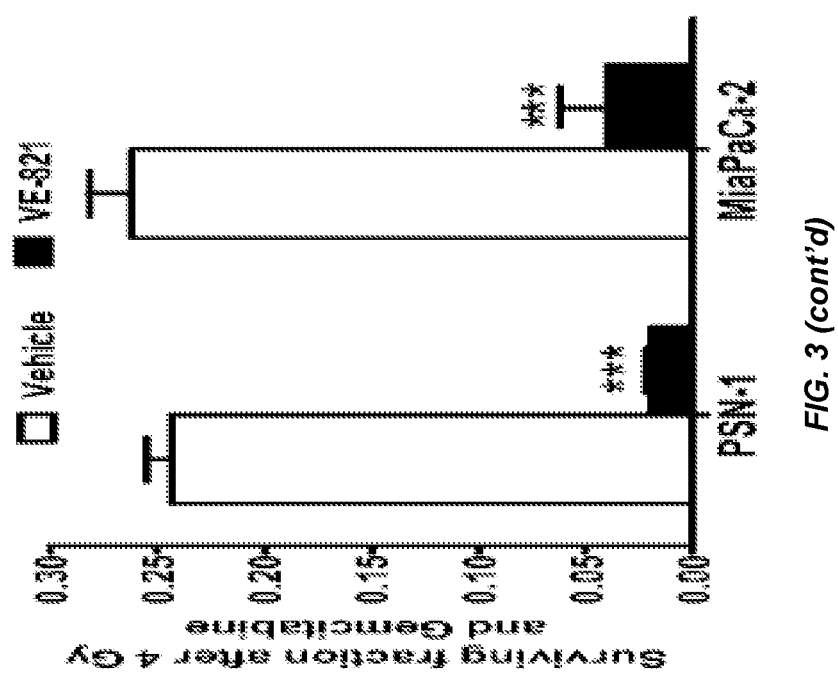
Figure 4:
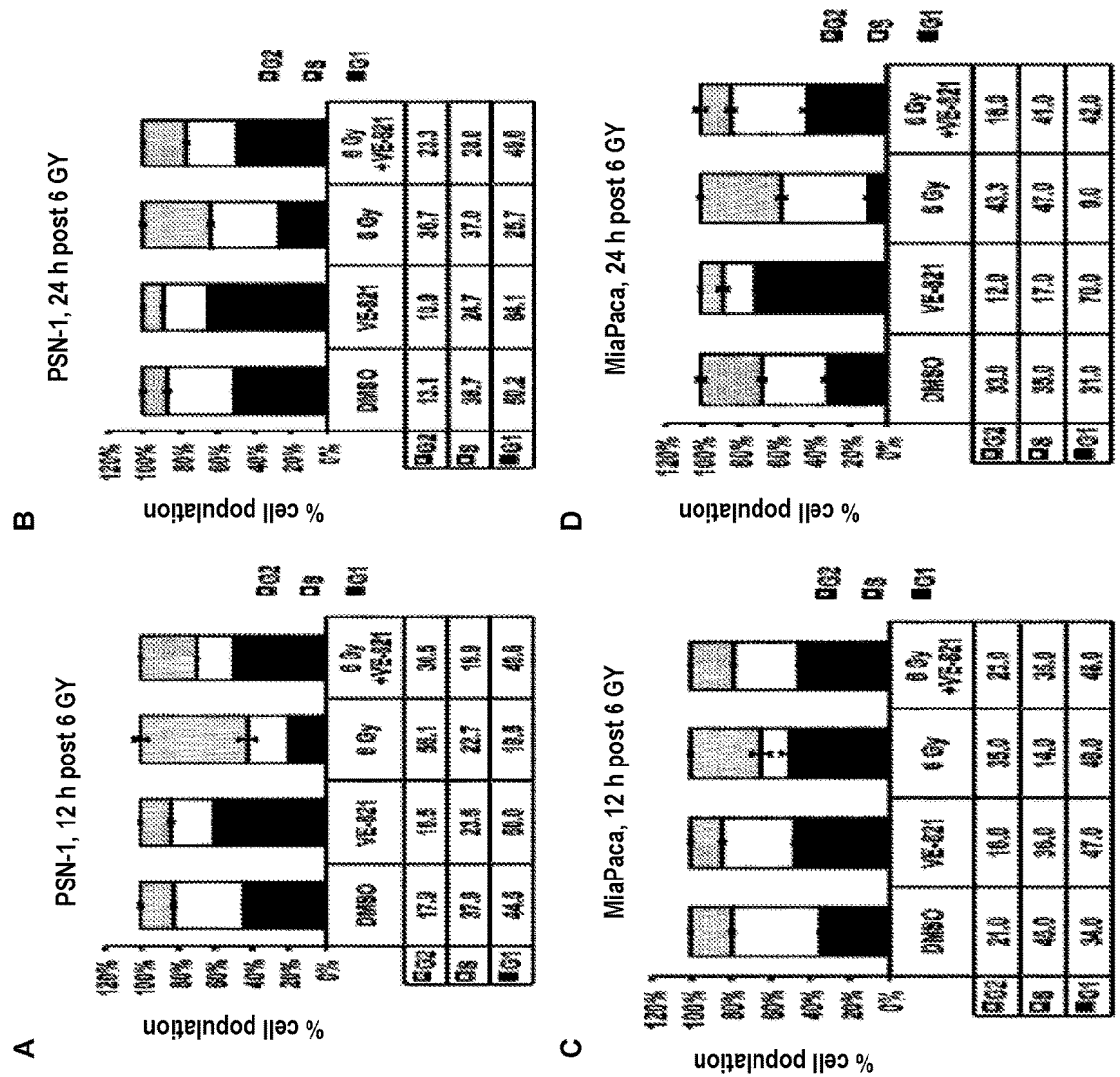
FIG. 4. VE-821 perturbs the irradiation-induced cell cycle checkpoint in pancreatic cancer cells.
VE-821 (1 µM) was added 1 h prior to 6 Gy irradiation and left for the duration of the experiment. Cells were lifted and fixed at 12 h or 24 h after irradiation, stained with propidium iodide and analysed for cell cycle distribution by flow cytometry (n=3)
FIG. 5. VE-821 increases 53BP1 and γH2AX foci number and reduces RAD51 foci formation.
Cells were treated with 1 µM VE-821 at various time points in relation to 6 Gy irradiation, as indicated, and fixed at 24 h post-irradiation. Subsequently, cells were stained for (A) γH2AX and (B) 53BP1 foci and the percentage of cells with more than 7 and 5 foci per cell was quantitated, respectively. C, for analysing Rad51 foci formation, cells were fixed at 6 h post-irradiation and the percentage of cells with more than 9 foci per cell was quantitated. Representative images are shown on the right (n=3). *, $P<0.05$
FIG. 6. Effect of VE-821 incubation time on plating efficiency.
PSN-1 cells were plated as single cells, treated with luM VE-821 for various time periods and assessed for colony formation after 10 days.
Figure 5:
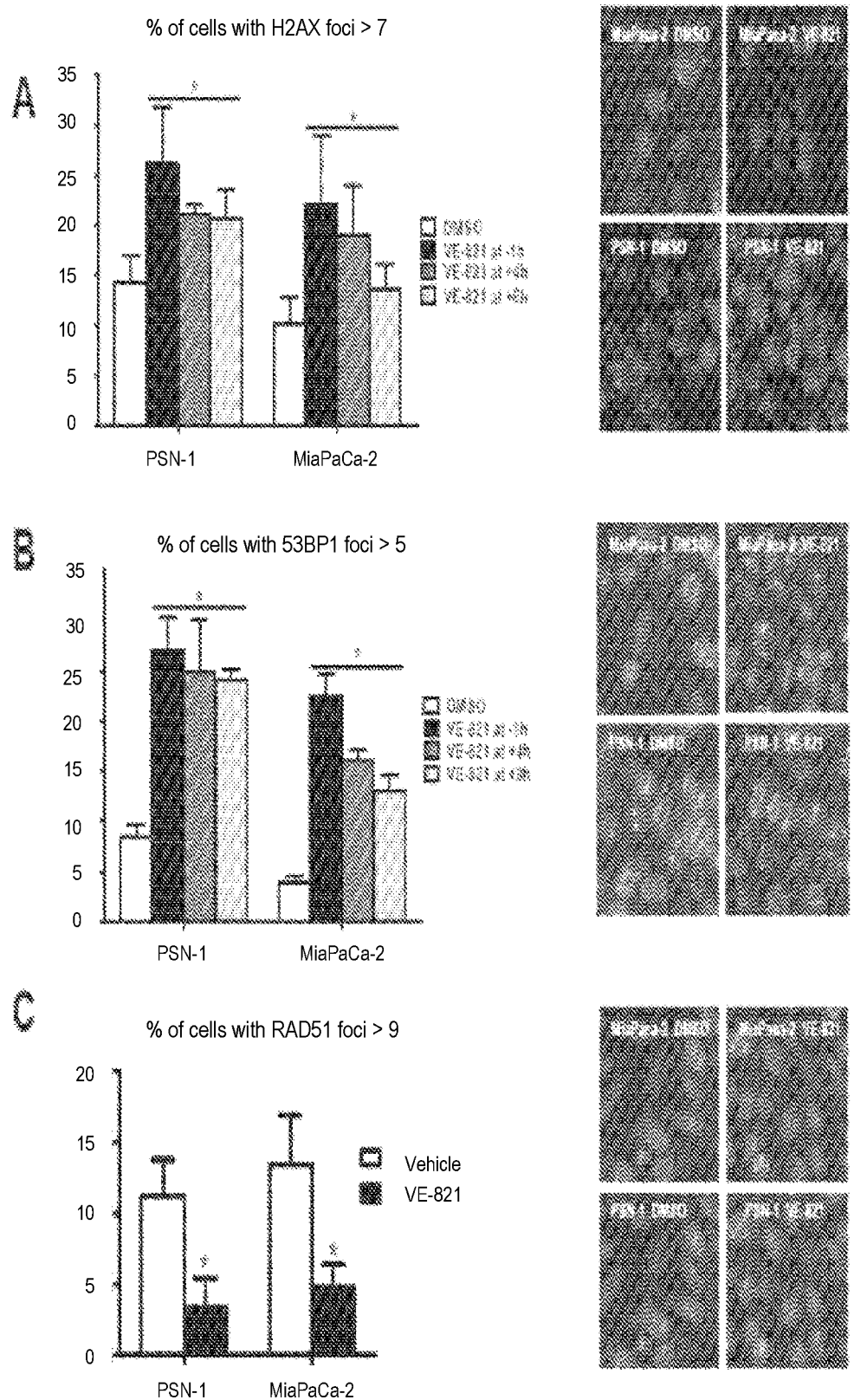
Figure 6:
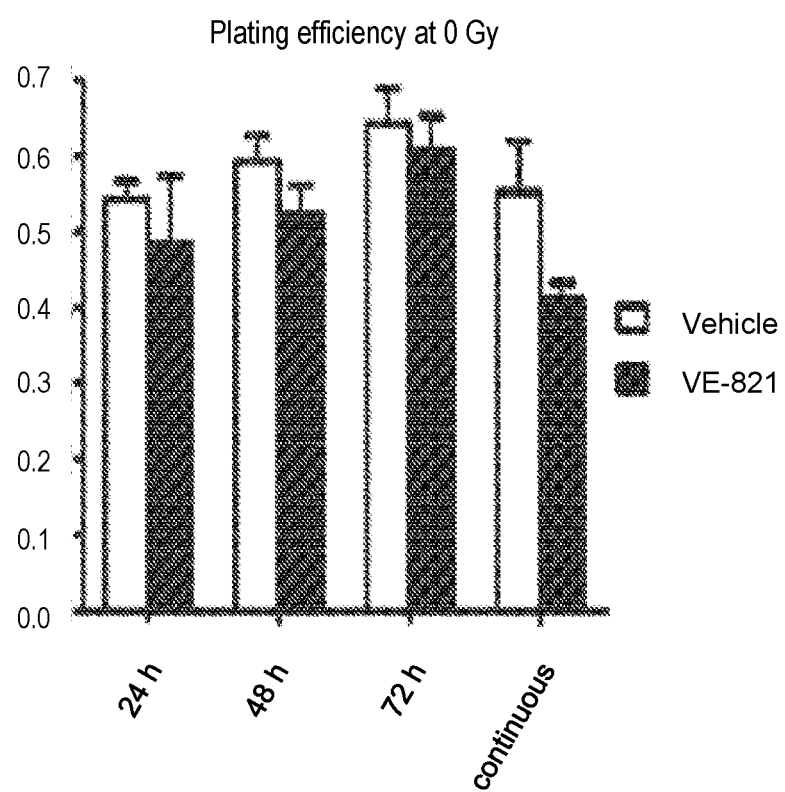
Figure 7:
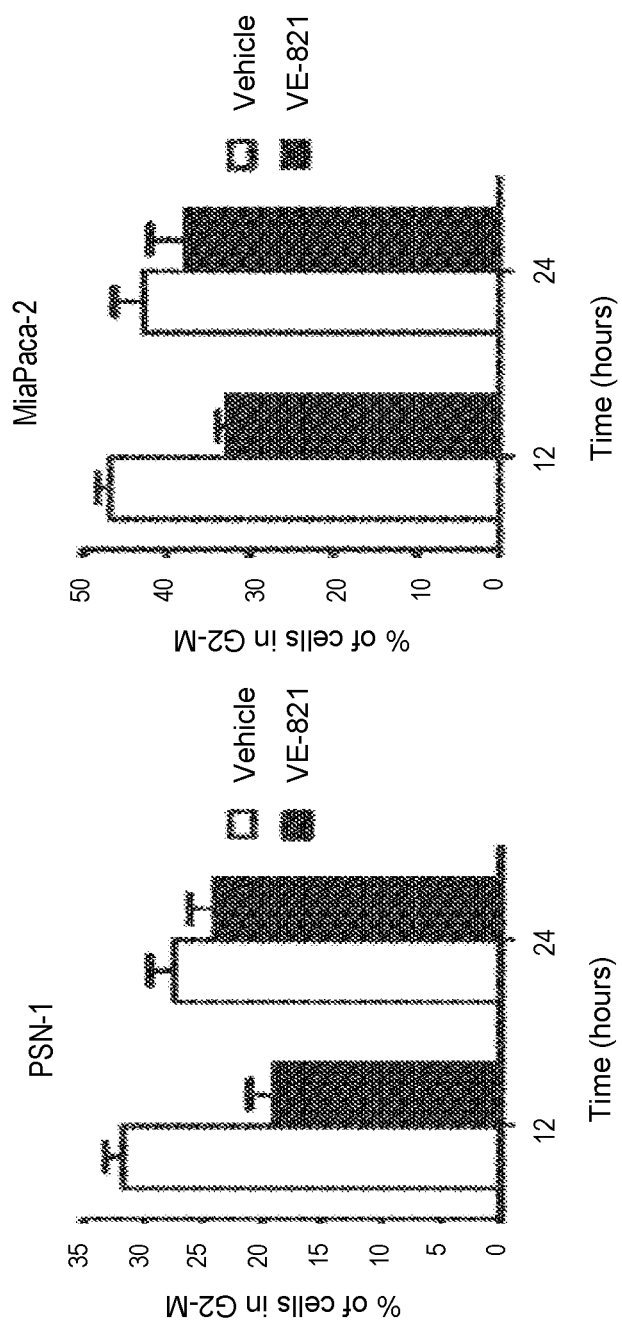
FIG. 7.
VE-821 perturbs the irradiation-induced G2/M checkpoint in pancreatic cancer cells in hypoxic conditions.
Cells were pre-incubated under hypoxic (0.5% $O_2$) conditions for 6 h and 1 µM VE-821 was added 1 h prior to irradiation (6 Gy). Cells were transferred to normoxia 1 h after irradiation and were lifted and fixed at 12 h or 24 h after irradiation, stained with propidium iodide and analysed for cell cycle distribution by flow cytometry (n=3).
Figure 8:
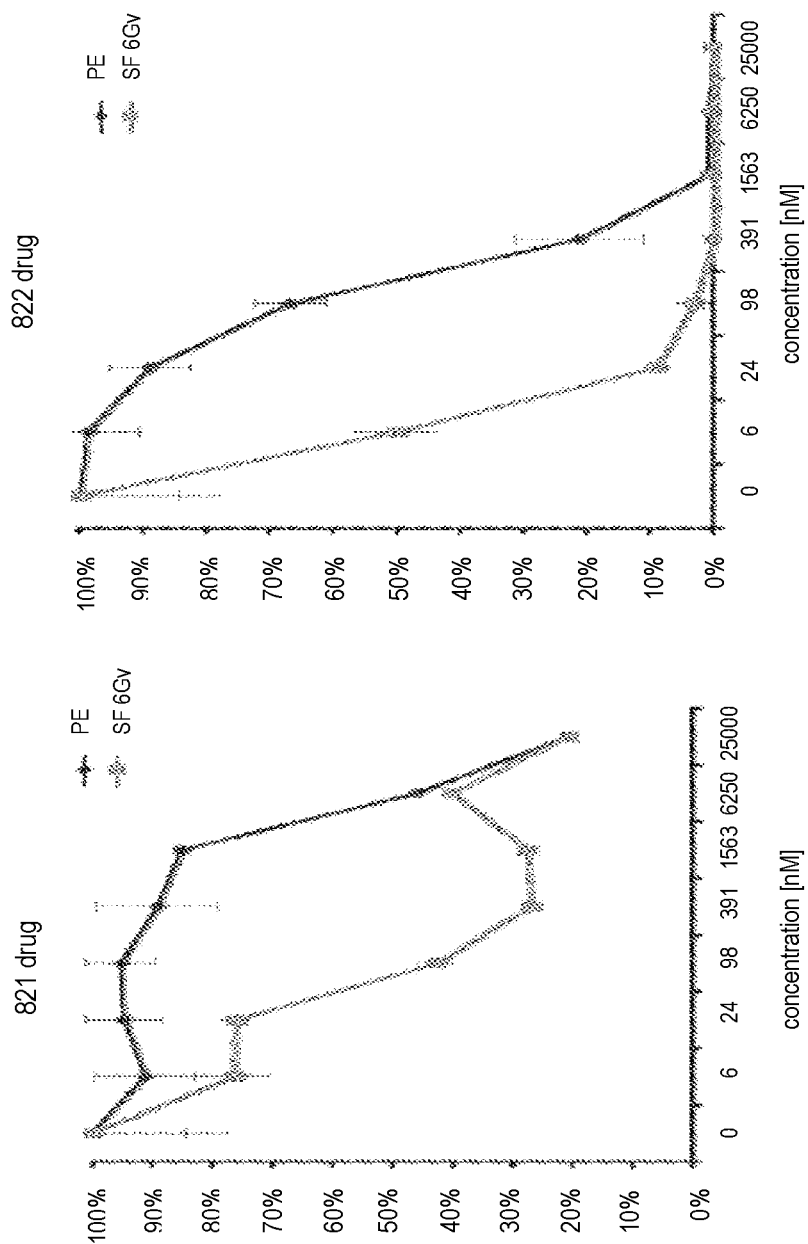
FIG. 8. Dose response relationship for radiosensitivity induced by Compounds 821, 822, 823, and 824.
Small scale clonogenic survival assays were performed on HeLa cells treated with the different ATR inhibitors at increasing concentrations followed by irradiation at 6 Gy. Data is plotted as decrease in clonogenic survival in relation to the DMSO-treated cells for both irradiated (SF 6 Gy, pink line) and unirradiated cells (plating efficiency, PE; blue line). A high degree of increased radiosensitivity can be seen as a large decrease in survival after irradiation accompanied by a small decrease in unirradiated survival at a specific drug concentration.
Figure 8:
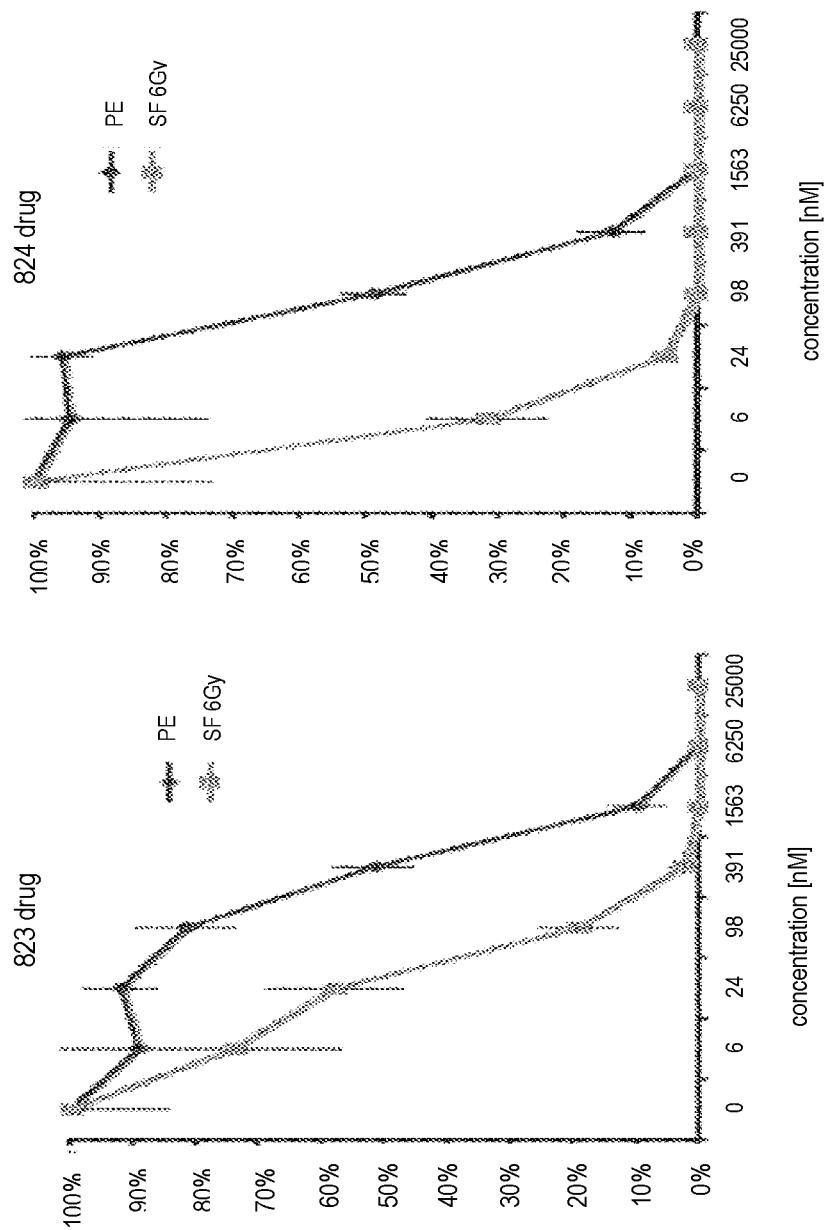
Figure 9:
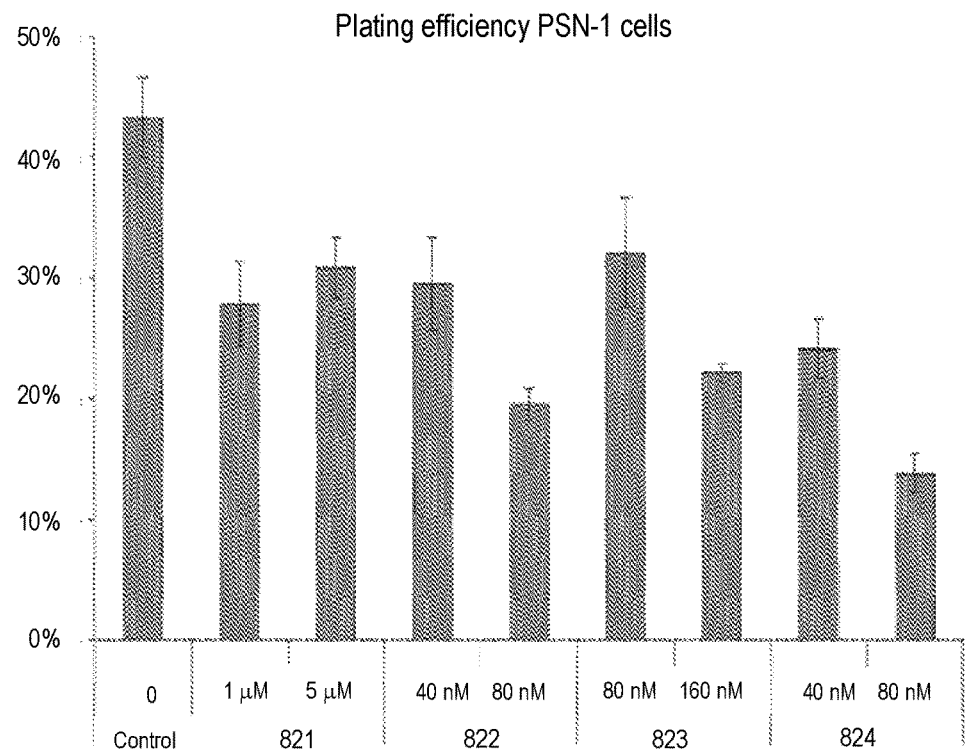
FIG. 9. Assessment of radiosensitivity in tumour cells and normal cells.
  A) Clonogenic survival after drug treatment in the absence of irradiation. PSN1 and MiaPaca cells were plated at low densities, treated with the drugs indicated and assessed for clonogenic survival.
  B) Clonogenic survival of PSN1, MiaPaca, and MRCS cells pretreated with Compounds 821, 822, 823 and 824 drugs followed by irradiation. Cells were plated at low densities, treated with drugs indicated 1 h prior to irradiation and assessed for clonogenic survival.
Figure 9:
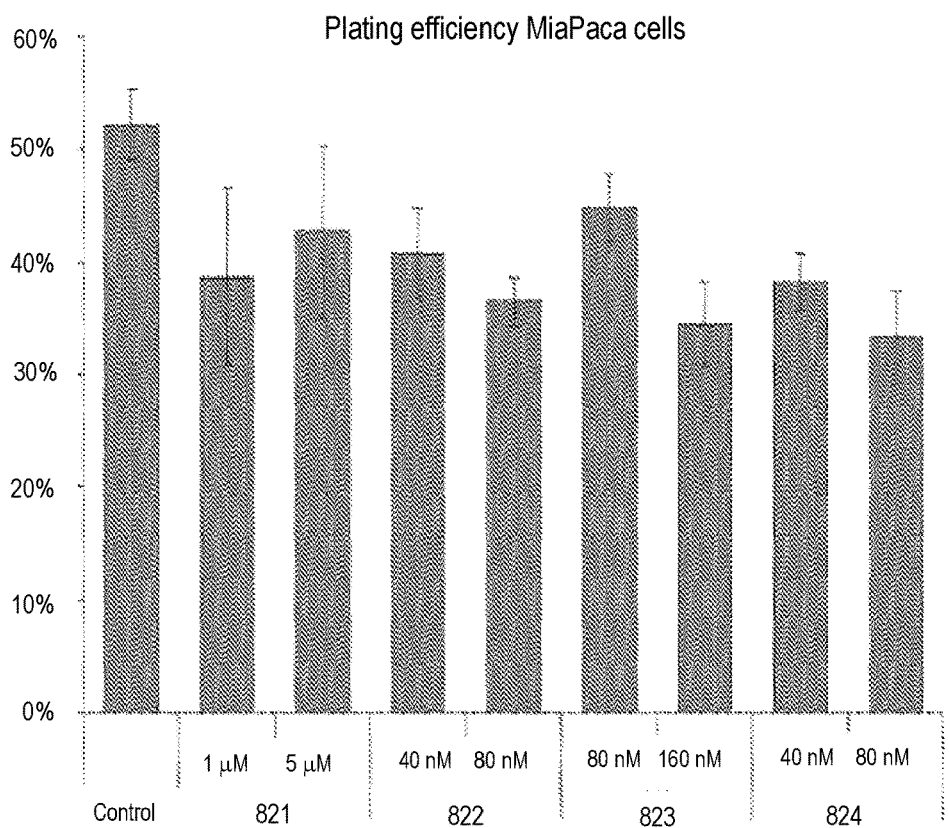
Figure 9:
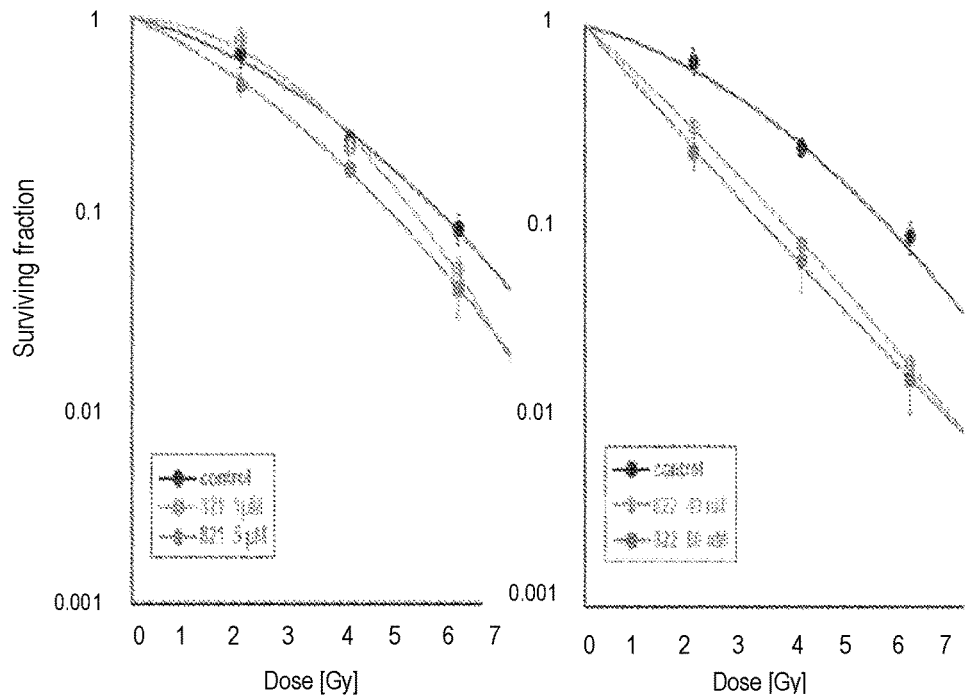
Figure 9:
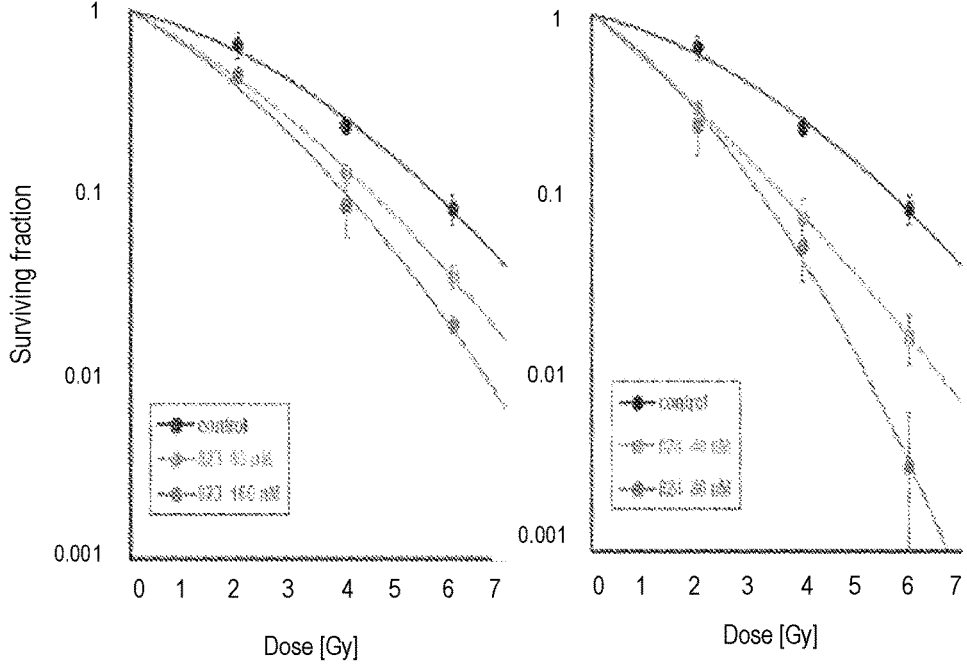
Figure 9:
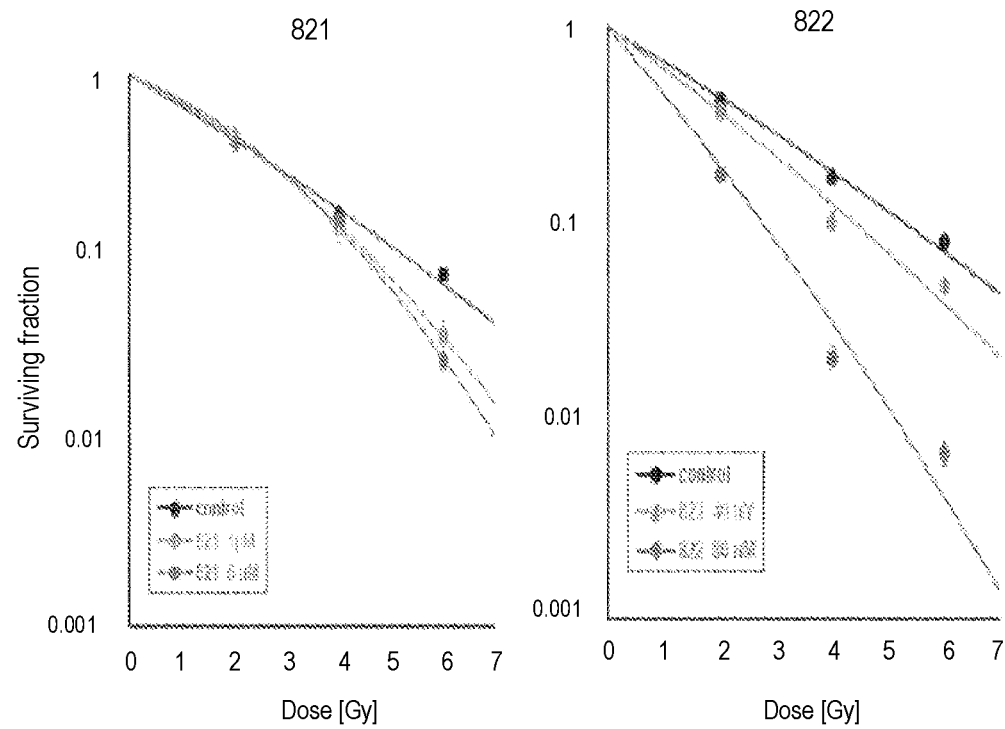
Figure 9:
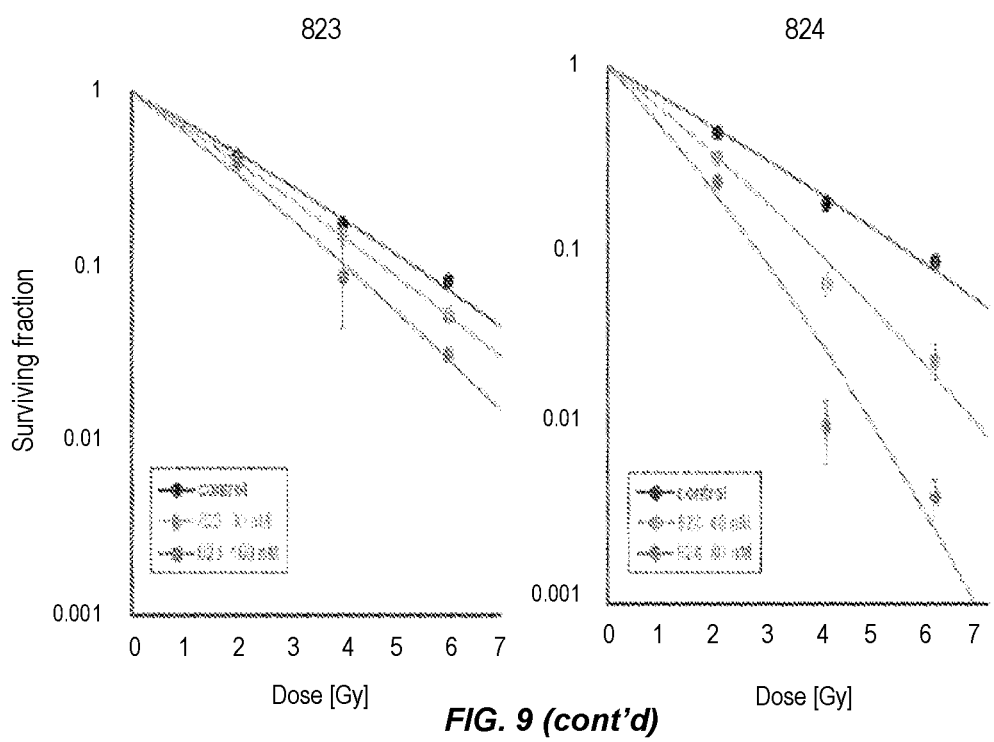
Figure 9:
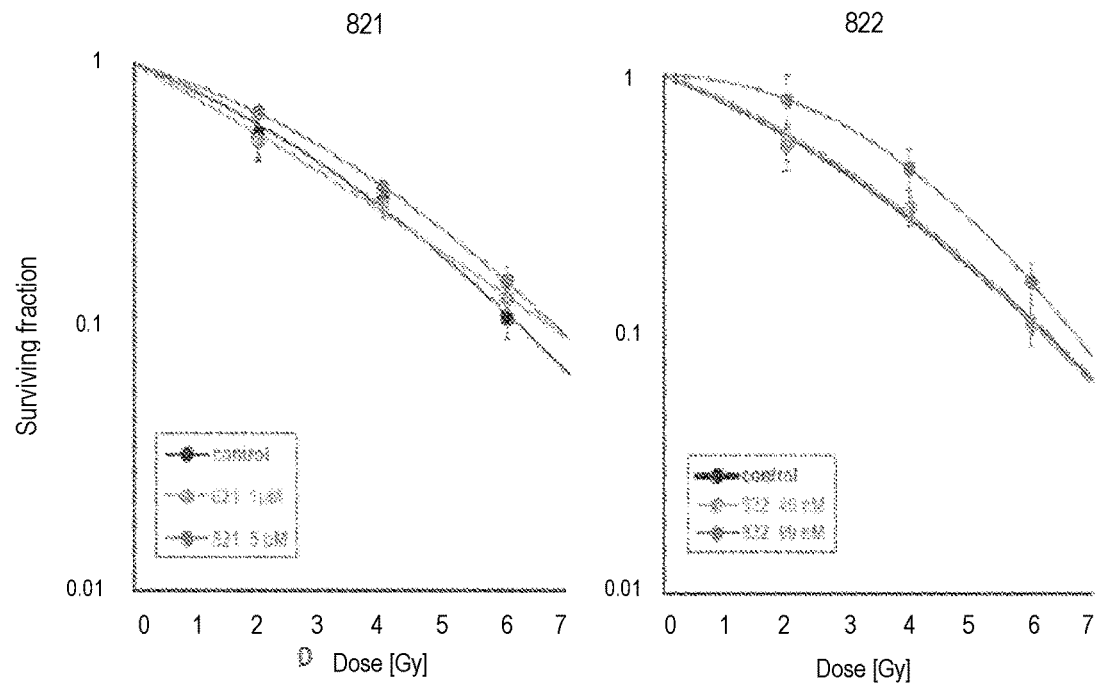
Figure 9:
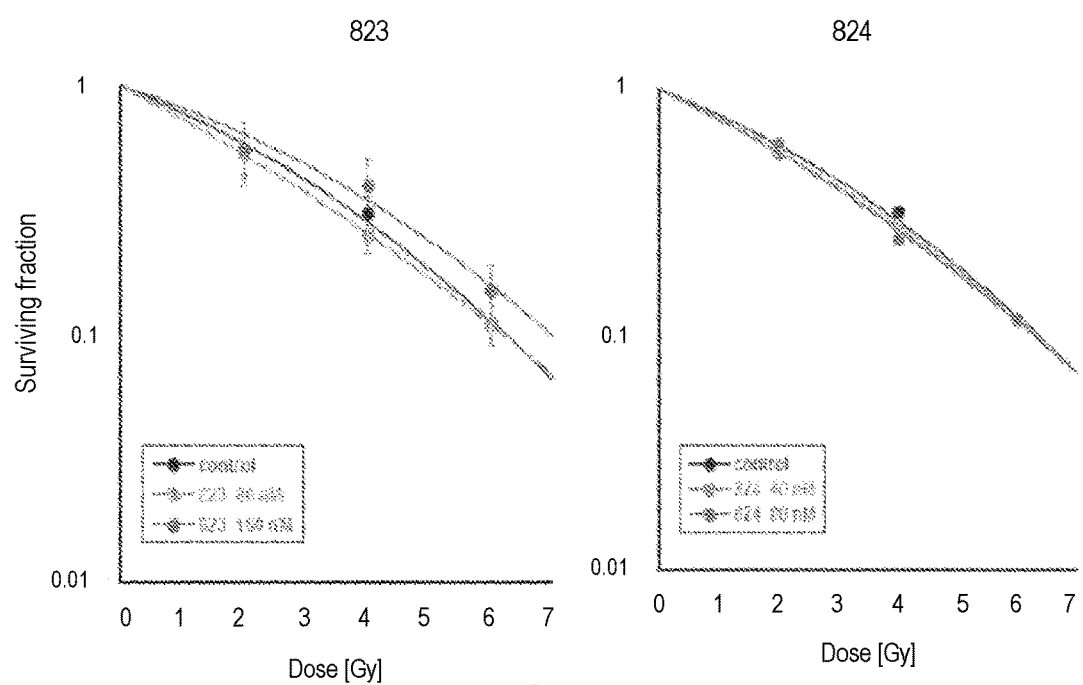
Figure 10:
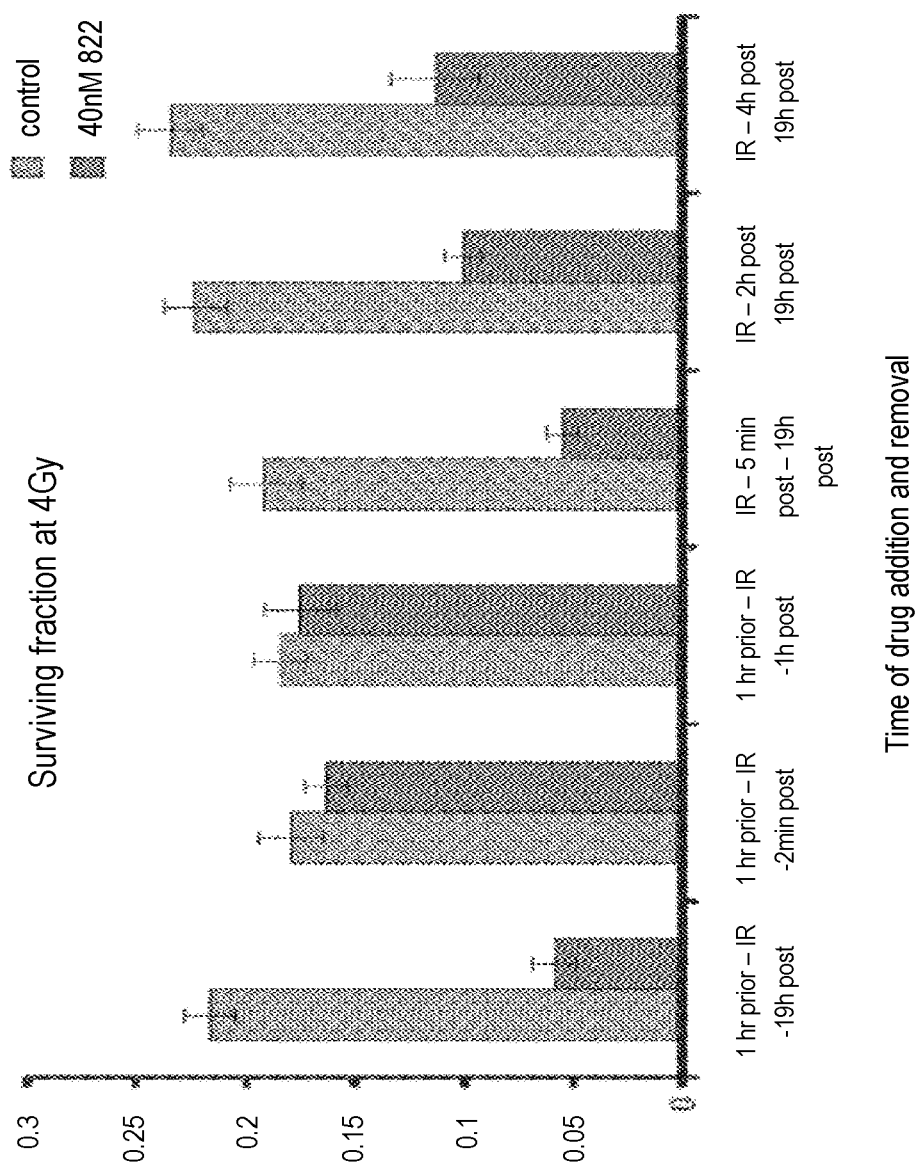
FIG. 10. Assessment of dependency of drug addition and removal timing on radiosensitivity.
Figure 10:
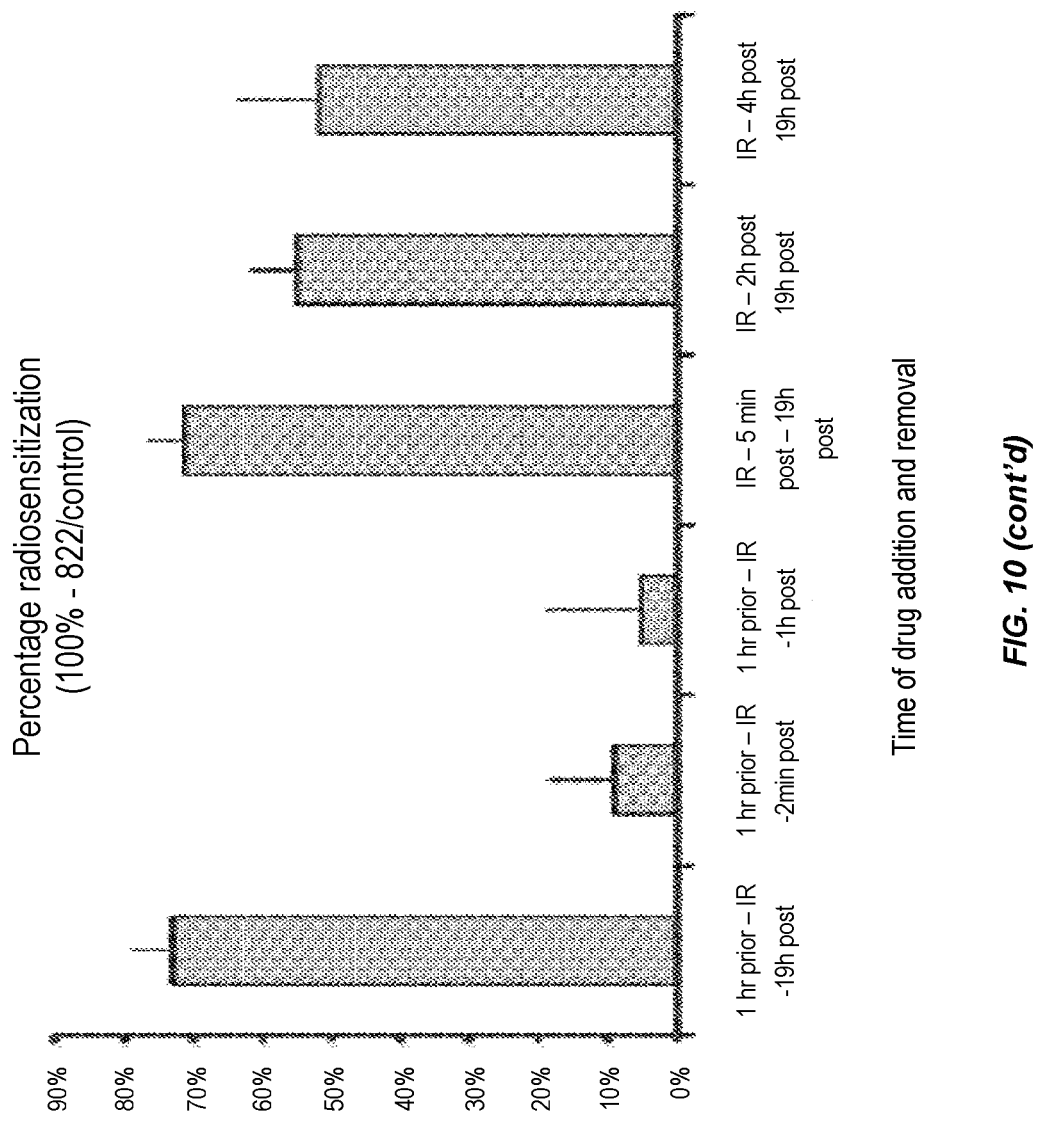
Figure 10:
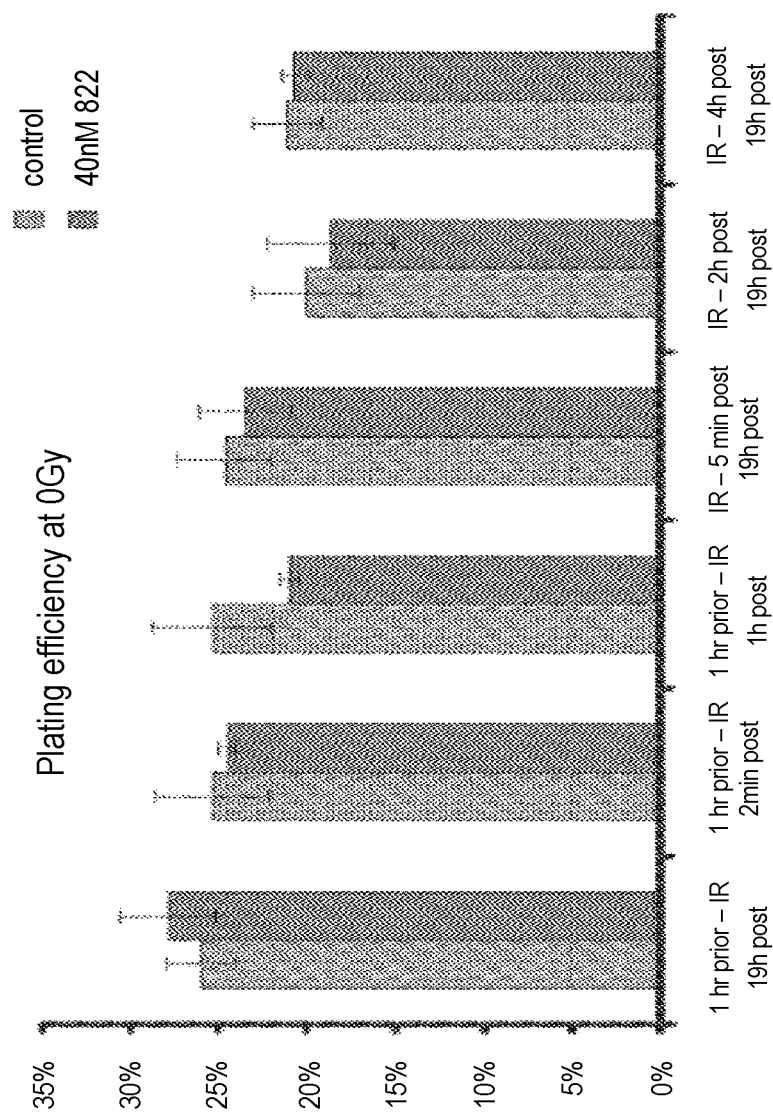

Compound VE-821 radiosensitises tumour PSN-1, MiaPaCa-2 and PancM cells under hypoxic conditions (see FIG. 2, panels A-B). Compound VE-821 also sensitises normoxic and hypoxic cancer cells to gemcitabine (see FIG. 3, panels B-C). Compound VE-821 potentiates the effect of chemoradiation in both PSN-1 and MiaPaCa-2 cancer cells (see FIG. 3, panel D). Compound VE-821 disrupts damage-induced cell cycle checkpoints (see FIG. 7). Compound VE-821 inhibits repair of DNA damage by homologous recombination (see FIG. 5, panels A, B, and C).

Results for Compounds 821 and 822 are shown in FIGS. 8 to 15 and FIGS. 16 to 21. VE-821 and VE-822 sensitize cancer cells to radiation therapy (see FIGS. 8 to 12).

VE-822 Enhances the Antitumor Effects of Cancer Therapies in Xenograft Models

VE-822 enhances the antitumor effects of ionizing radiation in a MiaPaCa pancreatic cancer xenograft model (see FIG. 13) and in a PSN-1 pancreatic cancer xenograft model (see FIGS. 14 and 15).

Figure 20:
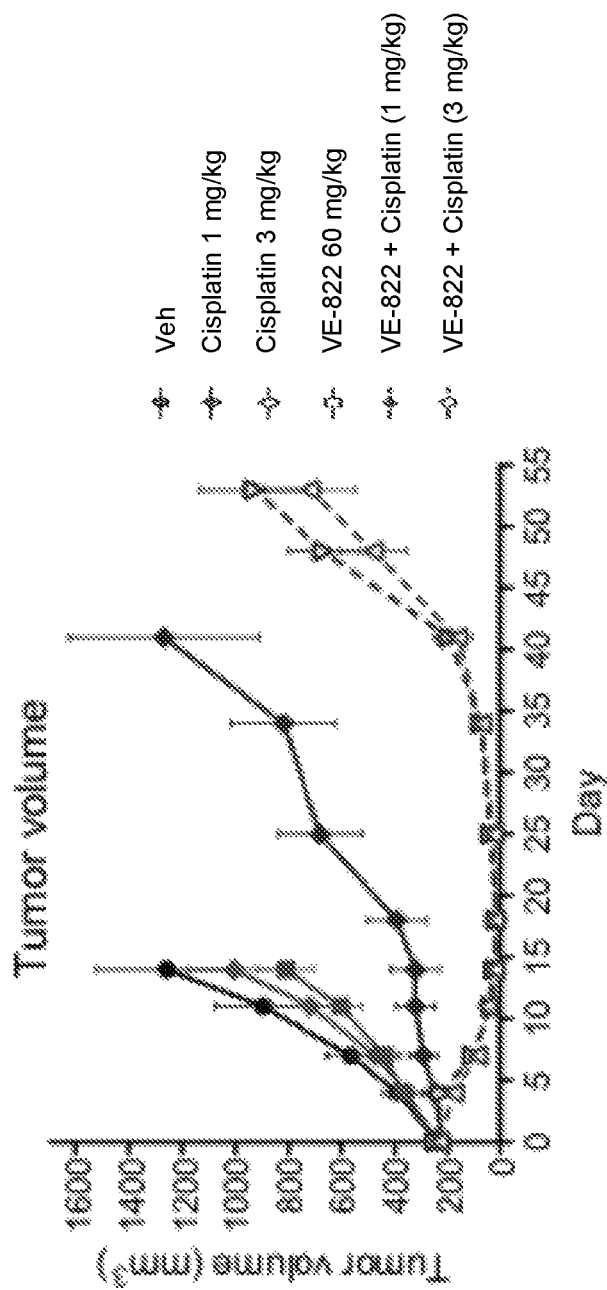

VE-822 enhances the antitumor effects of cisplatin in a primary adenocarcinoma NSCLC xenograft model. FIG. 20 shows the effect of VE-822 and cisplatin on tumor volume and body weight in a primary adenocarcinoma NSCLC xenograft in SCID mice. Data are mean±sem, n=9-10. Black filled circles are vehicle treatment; Red filled diamonds are Cisplatin treatment (1 mg/kg q7d); Blue filled diamonds are Cisplatin treatment (3 mg/kg q7d); Green filled squares are VE-822 treatment (60 mg/kg qd4); Green empty triangles are Cisplatin (1 mg/kg) and VE-822 (60 mg/kg qd4); Blue empty triangles are Cisplatin (3 mg/kg) and VE-822 (60 mg/kg qd4) (see FIG. 20).

VE-822 also enhances the antitumor effects of gemcitabine in a PSN1 pancreatic cancer xenograft model. FIG. 21 shows the effect of VE-822 administered PO q2d at 10, 30 or 60 mg/kg in combination with gemcitabine (15 mg/kg IP q3d) on the tumor volume of mice bearing PSN1 pancreatic cancer xenografts. Data shown are mean tumor volume±SEM (n=8 per group). Red filled circles are VE-822 treatment; Black filled squares are vehicle treatment; Green filled circles are gemcitabine treatment; Blue filled circles are gemcitabine and VE-822 (10 mg/kg) treatment; Red filled circles are gemcitabine and VE-822 (30 mg/kg) treatment; Pink filled circles are gemcitabine and VE-822 (60 mg/kg) treatment;

VE-822 Synergizes with Chemotoxics Across a Panel of Lung Cancer Cell Lines

The heat map represents the maximum shift in $IC_{50}$ of each chemotoxic achieved when combined with VE-822 for 96 hours. Colors represent an $IC_{50}$ shift range from −10 (antagonism, blue) to 10 (synergy, red) (see FIG. 16). VE-822 exhibits greater than 3-fold synergy with cisplatin, etoposide, gemcitabine, oxaplatin and irinotecan in lung cancer cell lines (see FIG. 17).

VE-822 Synergizes with Cisplatin and Gemcitabine in Pancreatic Cancer Cell Lines.

The heat map represents the maximum shift in $IC_{50}$ of each chemotoxic achieved when combined with VE-822 for 96 hours. Colors represent an $IC_{50}$ shift range from −10 (antagonism, blue) to 10 (synergy, red) (see FIG. 18).

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

The invention claimed is:

1. A method of treating non-small cell lung cancer in a patient, comprising administering to a patient with non-small cell lung cancer a therapeutic amount of compound 822:

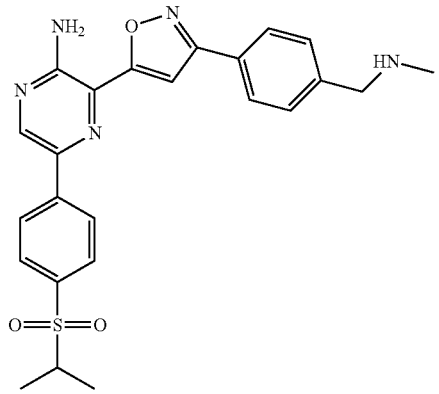

or a composition thereof, and Etoposide.

* * * * *